US011285250B2

(12) United States Patent
Nguyen et al.

(10) Patent No.: US 11,285,250 B2
(45) Date of Patent: Mar. 29, 2022

(54) SYSTEMS AND METHODS FOR SEPARATING BLOOD UNDER CONDITIONS OF REDUCED PLASMA CLARITY

(71) Applicant: Fenwal, Inc., Lake Zurich, IL (US)

(72) Inventors: Lan T. Nguyen, Vernon Hills, IL (US); Jonathan W. Prendergast, Palatine, IL (US); Zahra R. Ali, Chicago, IL (US); Tanima J. Abedin, Chicago, IL (US); Molly Erickson, Colorado Springs, CO (US); Korri Hershenhouse, Glenview, IL (US)

(73) Assignee: Fenwal, Inc., Lake Zurich, IL (US)

( * ) Notice: Subject to any disclaimer, the term of this patent is extended or adjusted under 35 U.S.C. 154(b) by 663 days.

(21) Appl. No.: 15/912,893

(22) Filed: Mar. 6, 2018

(65) Prior Publication Data
US 2018/0256805 A1 Sep. 13, 2018

Related U.S. Application Data

(60) Provisional application No. 62/467,869, filed on Mar. 7, 2017.

(51) Int. Cl.
*A61M 1/34* (2006.01)
*B01D 21/26* (2006.01)
(Continued)

(52) U.S. Cl.
CPC ........ *A61M 1/3496* (2013.01); *A61M 1/0272* (2013.01); *A61M 1/3681* (2013.01);
(Continued)

(58) Field of Classification Search
CPC .............. A61M 1/0272; A61M 1/3496; A61M 1/3681; A61M 1/3693; A61M 1/38;
(Continued)

(56) References Cited

U.S. PATENT DOCUMENTS 5,316,667 A * 5/1994 Brown ................... B01D 21/26
  210/85
5,632,893 A 5/1997 Brown et al.
(Continued)

FOREIGN PATENT DOCUMENTS

EP 0682953 A1 11/1995
EP 1295619 A2 3/2003
(Continued)

OTHER PUBLICATIONS

Partial European Search Report, dated Jul. 25, 2018, for application No. EP 18160084.2-1115.

*Primary Examiner* — Dirk R Bass
(74) *Attorney, Agent, or Firm* — Cook Alex Ltd.

(57) ABSTRACT

Blood separation systems and methods are provided for separating blood under conditions of reduced plasma clarity. The system may assess plasma clarity by monitoring light transmissivity of plasma or comparing an actual plasma flow rate to an ideal plasma flow rate, with a low flow rate indicating decreased clarity, which may be addressed by increasing the plasma flow rate. For extracorporeal photopheresis, plasma clarity may be a factor in determining the dosage of irradiating light to apply to mononuclear cells. A fluid processing assembly for mononuclear cell collection may include visual indicium, which an operator may use to determine when to end mononuclear cell collection. The system may detect red blood cells flowing toward a mononuclear cell collection container and reverse the direction of flow to prevent red blood cells from entering the container.

(Continued)

An operator may also be enabled to selectively begin and/or end harvesting of mononuclear cells.

21 Claims, 10 Drawing Sheets

(51) Int. Cl.
 G01N 33/49 (2006.01)
 G01N 35/00 (2006.01)
 B01L 3/00 (2006.01)
 A61M 1/36 (2006.01)
 A61M 1/02 (2006.01)
 A61M 1/38 (2006.01)

(52) U.S. Cl.
 CPC ............ *A61M 1/3693* (2013.01); *A61M 1/38* (2013.01); *B01L 3/502* (2013.01); *G01N 33/491* (2013.01); *G01N 35/0092* (2013.01); *A61M 2202/0415* (2013.01); *A61M 2202/0439* (2013.01); *A61M 2205/12* (2013.01); *A61M 2205/18* (2013.01); *A61M 2205/3303* (2013.01); *A61M 2205/3306* (2013.01); *B01D 21/262* (2013.01); *B01L 2200/0652* (2013.01); *B01L 2300/123* (2013.01); *B01L 2400/06* (2013.01); *G01N 2035/00495* (2013.01)

(58) Field of Classification Search
 CPC .. A61M 2202/0415; A61M 2202/0439; A61M 2205/12; A61M 2205/18; A61M 2205/3303; A61M 2205/3306; B01D 21/262; B01L 2200/0652; B01L 2300/123; B01L 2400/06; B01L 3/502; G01N 2035/00495; G01N 33/491; G01N 35/0092
 See application file for complete search history.

(56) References Cited

U.S. PATENT DOCUMENTS

| | | | |
|---|---|---|---|
| 5,676,644 A * | 10/1997 | Toavs | A61M 1/3692 604/6.11 |
| 5,774,059 A | 6/1998 | Henry et al. | |
| 5,868,696 A | 2/1999 | Giesler et al. | |
| 5,961,842 A | 10/1999 | Min et al. | |
| 5,980,760 A * | 11/1999 | Min | B01D 21/262 210/782 |
| 5,984,887 A | 11/1999 | McLaughlin et al. | |
| 6,254,784 B1 | 7/2001 | Nayak et al. | |
| 6,312,607 B1 | 11/2001 | Brown et al. | |
| 8,556,793 B2 * | 10/2013 | Foley | A61M 1/3693 494/37 |
| 2004/0223857 A1 | 11/2004 | Kline et al. | |
| 2005/0051466 A1 | 3/2005 | Carter et al. | |
| 2009/0129976 A1 | 5/2009 | Hoshino et al. | |
| 2010/0026986 A1 * | 2/2010 | Stanton | G01N 33/491 356/39 |
| 2012/0199539 A1 | 8/2012 | Foley et al. | |
| 2013/0197419 A1 * | 8/2013 | Min | B04B 11/02 604/6.01 |
| 2013/0317420 A1 | 11/2013 | Wehmeyer | |
| 2014/0057771 A1 | 2/2014 | Case et al. | |
| 2014/0228655 A1 | 8/2014 | Miller | |
| 2015/0219558 A1 | 8/2015 | Koudelka et al. | |
| 2016/0114095 A1 | 4/2016 | Radwanski | |
| 2016/0114339 A1 | 4/2016 | Nguyen et al. | |

FOREIGN PATENT DOCUMENTS

| | | |
|---|---|---|
| EP | 1640027 A1 | 3/2006 |
| EP | 2484391 A1 | 8/2012 |
| ER | 3124063 A1 | 2/2017 |
| WO | WO 99/01197 A1 | 1/1999 |
| WO | WO 99/01225 A1 | 1/1999 |
| WO | WO 2007/001754 A1 | 1/2007 |
| WO | WO 2012/091720 A1 | 7/2012 |

* cited by examiner

SYSTEMS AND METHODS FOR SEPARATING BLOOD UNDER CONDITIONS OF REDUCED PLASMA CLARITY

This application claims the benefit of and priority of U.S. Provisional Patent Application Ser. No. 62/467,869, filed Mar. 7, 2017, the contents of which are incorporated by reference herein.

BACKGROUND

Field of the Disclosure

The invention relates to blood separation systems and methods. More particularly, the invention relates to systems and methods for separating blood when plasma clarity is reduced.

BACKGROUND

Description of Related Art

Various blood processing systems now make it possible to collect particular blood constituents, rather than whole blood, from donors or patients or other blood sources. Typically, in such systems, whole blood is drawn from a source, the particular blood component or constituent is removed and collected, and the remaining blood constituents are returned to the source. By thus removing only particular constituents, potentially less time is needed for the source's body to return to normal (in the case of a living source), and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of a separation chamber included as part of the fluid processing assembly. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid processing assembly. For example, therapeutic plasma exchange involves separating plasma from cellular blood components, collecting the plasma, and returning the cellular blood components and a replacement fluid to the patient.

Proper separation requires, however, that the interface between the separated components be located within a particular zone between the high-G and low-G walls of the separation chamber. For example, when performing a therapeutic plasma exchange procedure, the interface between the plasma and the cellular blood components affects the performance of the system. If the interface is located too close to the low-G wall, then the collected plasma may become unduly populated or contaminated by cellular blood components. On the other hand, if the interface is located too far from the low-G wall, there may be no contamination of the plasma, but the separation efficiency of the system may be decreased with less plasma collected over time.

Various known centrifuges, such as those shown and described in U.S. Pat. Nos. 6,254,784 and 6,312,607 (which are incorporated herein by reference), are operable to automatically keep the interface within a desired zone as the centrifuge operates. Typically, the separation chamber of the fluid processing assembly is loaded between the bowl and spool of a centrifuge. A radially inwardly ramped surface is located on the radially outer wall of the separation channel in the bowl wall of the separation chamber. The interface between the generally dark, opaque red blood cell layer and the generally light, clear plasma layer appears as a line on the ramped surface. Where, exactly, the line appears on the ramped surface is a function of the position of the interface between the high-G and low-G walls of the separation chamber. Accordingly, the position of the line on the ramped surface can be used to gauge the position of the interface between the high-G and low-G walls.

Automatic control over the location of the interface has been achieved by sensing the position of the line on the ramped surface and thereafter adjusting the centrifuge operating parameters to place and keep the line within desired limits. In particular, by controlling the rate at which plasma is withdrawn from the separation chamber, the line can be "moved" up (radially inwardly) or down (radially outwardly) on the ramped surface, such as by decreasing or increasing the plasma flow rate. Typically, an optical sensor assembly is used to sense the position of the line on the ramped surface. As the centrifuge spins past the sensor, the sensor develops an electrical pulse having a width related to the position of the line on the ramped surface. As the line moves closer to the high g wall of the separation chamber, the pulse width increases. As the line moves closer to the low-G wall, the pulse width narrows. By sensing the width of the pulses developed by the optical sensor and thereafter using the pulse width to increase or decrease the rate at which plasma is withdrawn from the separation chamber, the line can be kept within desired positional limits on the ramped surface and the interface maintained in the desired radial position or range of positions.

U.S. Pat. No. 8,556,793 (which is incorporated herein by reference) describes a system employing two optical sensor assemblies. An interface optical sensor assembly monitors the location of the interface on the ramped surface, while an outlet optical sensor assembly monitors outlet tubing carrying separated plasma to assess various characteristics of the plasma flow (including turbidity and the concentration of free plasma hemoglobin).

Experience has shown that it is possible for the interface optical sensor assembly to detect a spillover condition (which is indicative of cellular components spilling into the separated plasma) while the outlet optical sensor assembly indicates that the plasma is sufficiently clear (i.e., that the cellular components have not spilled into the separated plasma). This may happen for any of a number of reasons, for example, due to the presence of cold agglutinins. Detection of a spillover condition may cause a temporary decrease in the plasma flow rate through the outlet tubing in order to relocate the interface on the ramped surface, which eliminates the spillover condition. However, if the outlet optical sensor assembly shows that the plasma is sufficiently clear, then the slowed plasma flow rate may only lengthen the procedure, rather than providing the intended benefit. An approach to reconciling such a conflict between the two optical sensor assemblies for safe, efficient blood processing is described in U.S. Pat. No. 9,895,700, which is incorporated herein by reference.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing system includes a blood separation chamber configured to separate mononuclear cells from a plasma constituent of blood. An outlet flow path is associated with the blood separation chamber for alternately removing at least a portion of the plasma constituent and at least a portion of the mononuclear cells from the blood separation chamber, with the outlet flow path including a valve station movable between first and second conditions to change the direction of flow of fluid through the outlet flow path. A mononuclear cell collection container is in fluid communication with the outlet flow path. A system controller is programmed to execute a mononuclear cell collection procedure including a build-up phase in which at least a portion of the plasma constituent flows through the outlet flow path and the controller causes the valve station to be in the first condition to direct the flow of the plasma constituent through the outlet flow path away from the mononuclear cell collection container while a volume of the mononuclear cells increases in the blood separation chamber. The procedure also includes harvest phase in which at least a portion of the mononuclear cells flows through the outlet flow path and the controller causes the valve station to be in the second condition to direct the flow of mononuclear cells through the outlet flow path to the mononuclear cell collection container, with the controller being programmed to allow an operator to selectively transition from the build-up phase to the harvest phase and/or from the harvest phase to the build-up phase substantially instantaneously.

In another aspect, a method is provided for collecting mononuclear cells. The method includes separating mononuclear cells from a plasma constituent of blood in a blood separation chamber and executing a build-up phase in which at least a portion of the plasma constituent flows out of the blood separation chamber via an outlet flow path with a valve station of the outlet flow path in a first condition to direct the flow of the plasma constituent through the outlet flow path away from a mononuclear cell collection container in fluid communication with the outlet flow path while a volume of the mononuclear cells increases in the blood separation chamber. A harvest phase is executed in which at least a portion of the mononuclear cells flows out of the blood separation via the outlet flow path with the valve station in a second condition to direct the flow of mononuclear cells through the outlet flow path to the mononuclear cell collection container, with an operator being enabled to selectively transition from the build-up phase to the harvest phase and/or from the harvest phase to the build-up phase substantially instantaneously.

In yet another aspect, a fluid processing system includes a blood separation chamber configured to separate a plasma constituent from another blood component, with an outlet port for removing at least a portion of the plasma constituent from the blood separation chamber. A system controller is programmed to calculate an ideal plasma flow rate for the plasma constituent flowing out of the blood separation chamber via the outlet port and compare the ideal plasma flow rate to a current plasma flow rate for the plasma constituent flowing out of the blood separation chamber via the outlet port. The controller determines that the plasma constituent has decreased clarity if the percent difference between the ideal plasma flow rate and the current plasma flow rate is greater than a threshold value, while determining that the plasma constituent does not have decreased clarity if the percent difference between the ideal plasma flow rate and the current plasma flow rate is less than the threshold value.

In another aspect, a method is provided for separating blood. The method includes separating a plasma constituent from another blood component in a blood separation chamber and flowing at least a portion of the plasma constituent out of the blood separation chamber at a current plasma flow rate. An ideal plasma flow rate is calculated for the plasma constituent flowing out of the blood separation chamber and compared to the current plasma flow rate. It is determined that the plasma constituent has decreased clarity if the percent difference between the ideal plasma flow rate and the current plasma flow rate is greater than a threshold value, whereas is it determined that the plasma constituent does not have decreased clarity if the percent difference between the ideal plasma flow rate and the current plasma flow rate is less than the threshold value.

In yet another aspect, a fluid processing assembly is configured for use in combination with a fluid processing system for separating mononuclear cells from red blood cells. The assembly includes a blood separation chamber configured to separate mononuclear cells from red blood cells, with an outlet port configured to accommodate the flow of mononuclear cells and then red blood cells exiting the blood separation chamber. An outlet flow path extends between the outlet port and a mononuclear cell collection container. The outlet flow path includes a visual indicium upstream of the mononuclear cell collection container positioned to indicate that fluid communication between the outlet flow path and the mononuclear cell collection container is to be prevented upon red blood cells flowing through the outlet flow path reaching a location identified by the visual indicium.

In another aspect, a method is provided for collecting mononuclear cells. The method includes separating mononuclear cells from red blood cells in a blood separation chamber and flowing at least a portion of the mononuclear cells out of the blood separation chamber via an outlet port, through an outlet flow path in fluid communication with the outlet port, and into a mononuclear cell collection container. At least a portion of the red blood cells is flowed out of the blood separation chamber via the outlet port and into the outlet flow path, with fluid communication between the outlet flow path and the mononuclear cell collection container being prevented when the red blood cells flowing through the outlet flow path reach a location identified by a visual indicium associated with the outlet flow path.

In yet another aspect, a fluid processing system includes a blood separation chamber configured to separate mononuclear cells from red blood cells. An outlet flow path is associated with the blood separation chamber and includes a rigid cassette and a flexible tubing in fluid communication with the cassette, downstream of the cassette. A mononuclear cell collection container is in fluid communication with the flexible tubing, downstream of the flexible tubing. A pump is configured to convey fluid through the outlet flow path, while a mononuclear cell optical sensor assembly is configured to monitor the flow of fluid through the flexible tubing. A controller is programmed to control the operation of the pump and the mononuclear cell optical sensor assembly. The mononuclear cell optical sensor assembly is configured to generate an output indicative of a transition from a flow of mononuclear cells through the flexible tubing toward the mononuclear cell collection container to a flow of red blood cells through the flexible tubing toward the mononuclear cell collection container. The controller is programmed to receive the output and control the pump to reverse the direction of flow of fluid through the flexible tubing to minimize the amount of red blood cells reaching the mononuclear cell collection container.

In another aspect, a method is provided for collecting mononuclear cells. The method includes separating mononuclear cells from red blood cells in a blood separation chamber and flowing at least a portion of the mononuclear cells out of the blood separation chamber via an outlet port, through a flexible tubing in fluid communication with the outlet port, and into a mononuclear cell collection container in fluid communication with the flexible tubing. At least a portion of the red blood cells is flowed out of the blood separation chamber via the outlet port and into the flexible tubing. The direction of flow of the red blood cells through the flexible tubing is reversed to minimize the amount of red blood cells reaching the mononuclear cell collection container.

In yet another aspect, a method is provided for collecting and treating mononuclear cells. The method includes separating mononuclear cells from a plasma constituent in a blood separation chamber and flowing at least a portion of the plasma constituent out of the blood separation chamber. It is determined whether the plasma constituent has decreased clarity. At least a portion of the mononuclear cells is flowed out of the blood separation chamber and into a mononuclear cell collection container. The mononuclear cells in the mononuclear cell collection container are irradiated with a dosage of light, with the dosage of light being equal to a default dosage if the plasma constituent does not have a decreased clarity and greater than the default dosage if the plasma constituent has decreased clarity.

In another aspect, a fluid processing system includes a blood separation chamber configured to separate mononuclear cells from a plasma constituent of blood, with an outlet flow path associated with the blood separation chamber. A mononuclear cell collection container is in fluid communication with the outlet flow path, while an irradiation device is configured to irradiate separated mononuclear cells in the mononuclear cell collection container. A controller is programmed to control the operation of the irradiation device and to determine whether the plasma constituent has decreased clarity. The controller controls the irradiation device to irradiate the separated mononuclear cells in the mononuclear cell collection container with a default dosage of light if the plasma constituent does not have decreased clarity, and control the irradiation device to irradiate the separated mononuclear cells in the mononuclear cell collection container with a dosage of light that is greater than the default dosage of light if the plasma constituent has decreased clarity.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail.

Therefore, specific designs and features disclosed herein are not to be interpreted as limiting the subject matter as defined in the accompanying claims.

Figure 1:
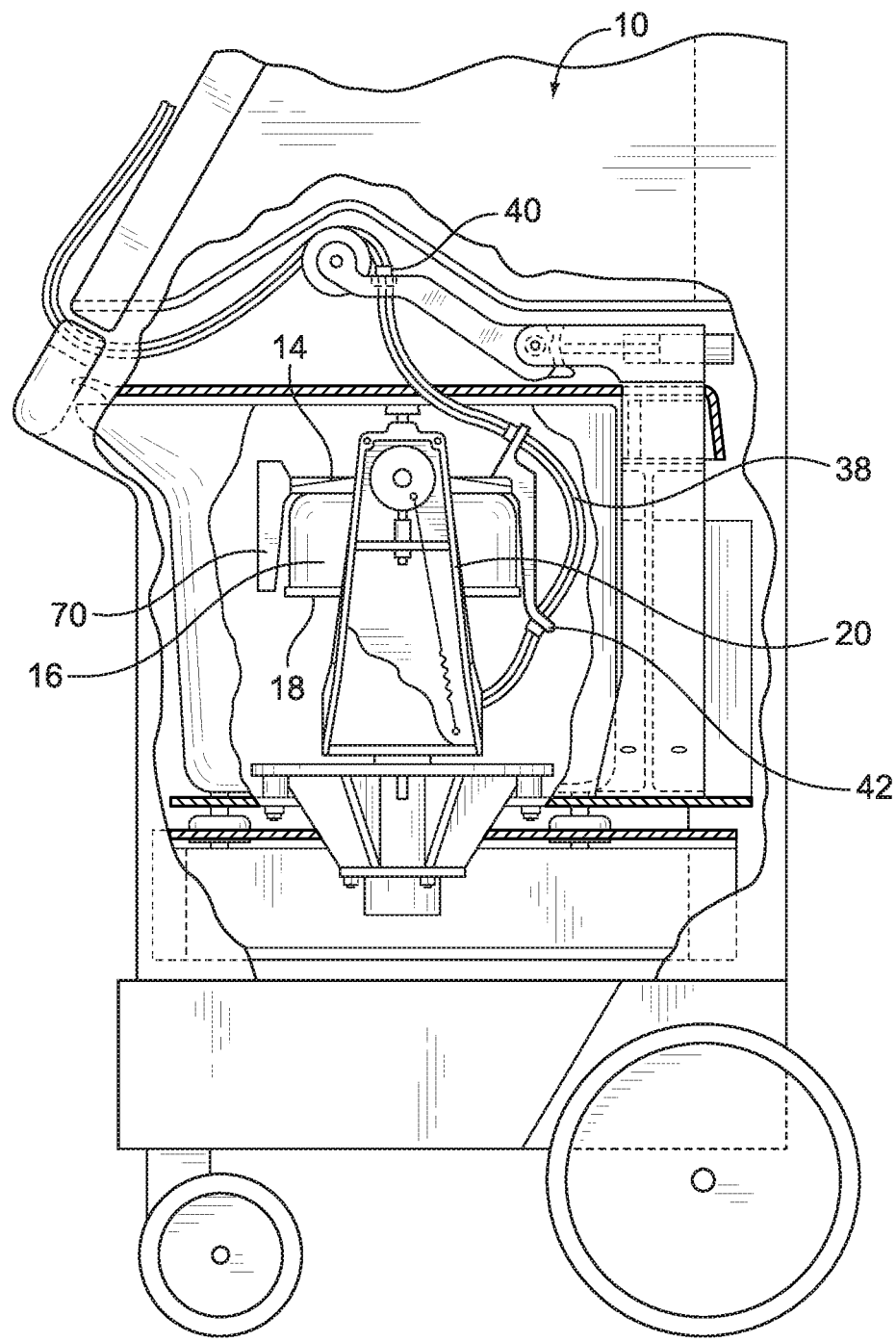
FIG. 1 is a side elevation view, with portions broken away and in section, of a centrifugal fluid processing system employing aspects of the present invention, with a centrifuge bowl and spool of the system being shown in their operating position.
Figure 2:
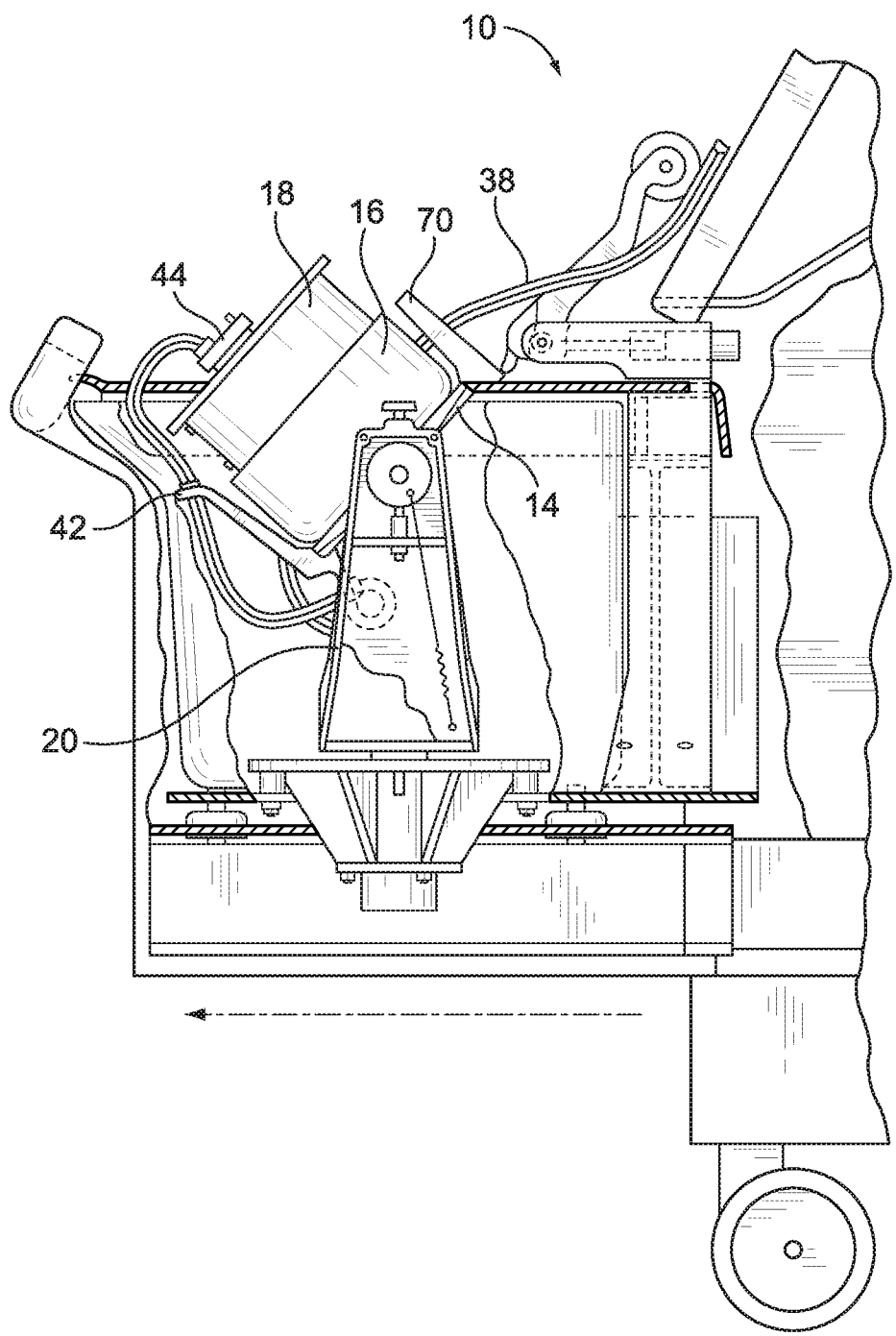
FIG. 2 is a side elevation view, with portions broken away and in section, of the system shown in FIG. 1, with the bowl and spool shown in an upright position for receiving a blood separation chamber.

FIGS. 1 and 2 show a centrifugal fluid processing system 10 with a system controller including an interface controller 12 (FIG. 11) that may be used in practicing the control principles of the present disclosure. The system is currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials. While interface control principles will be described herein with reference to one particular system 10, it should be understood that these principles may be employed with other fluid processing systems employing different interface control systems without departing from the scope of the present disclosure.

A. The Centrifuge

The system 10 includes a centrifuge 14 used to centrifugally separate blood components. The system 10 may be programmed to separate blood into a variety of components (e.g., platelet-rich plasma and red cells). For illustrative purposes, a mononuclear cell ("MNC") collection procedure, in which the centrifuge 14 separates and collects mononuclear cells (e.g., lymphocytes and monocytes) from whole blood, will be described herein. However, the principles described and claimed herein may be employed with other blood separation procedures without departing from the scope of the present disclosure.

The illustrated centrifuge 14 is of the type shown in U.S. Pat. No. 5,316,667 to Brown et al., which is incorporated herein by reference. The centrifuge comprises a bowl 16 and a spool 18. The bowl 16 and spool 18 are pivoted on a yoke 20 between an operating position (FIG. 1) and a loading/unloading position (FIG. 2).

When in the loading/unloading position, the spool 18 can be opened by movement at least partially out of the bowl 16, as FIG. 2 shows. In this position, the operator wraps a flexible blood separation chamber 22 (see FIG. 3) about the spool 18. Closure of the spool 18 and bowl 16 encloses the chamber 22 for processing. When closed, the spool 18 and bowl 16 are pivoted into the operating position of FIG. 1 for rotation about an axis.

B. The Blood Separation Chamber

Figure 4:
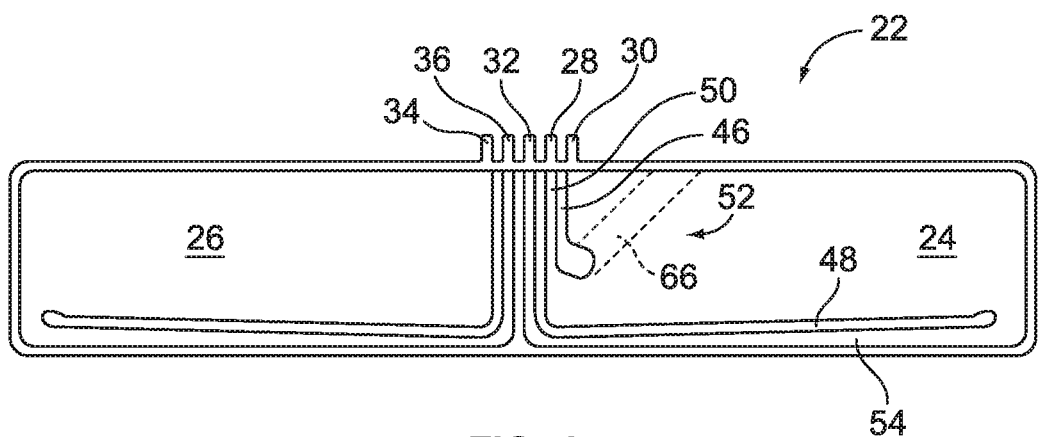
FIG. 4 is a plan view of the blood separation chamber shown in FIG. 3, out of association with the spool.
Figure 13:
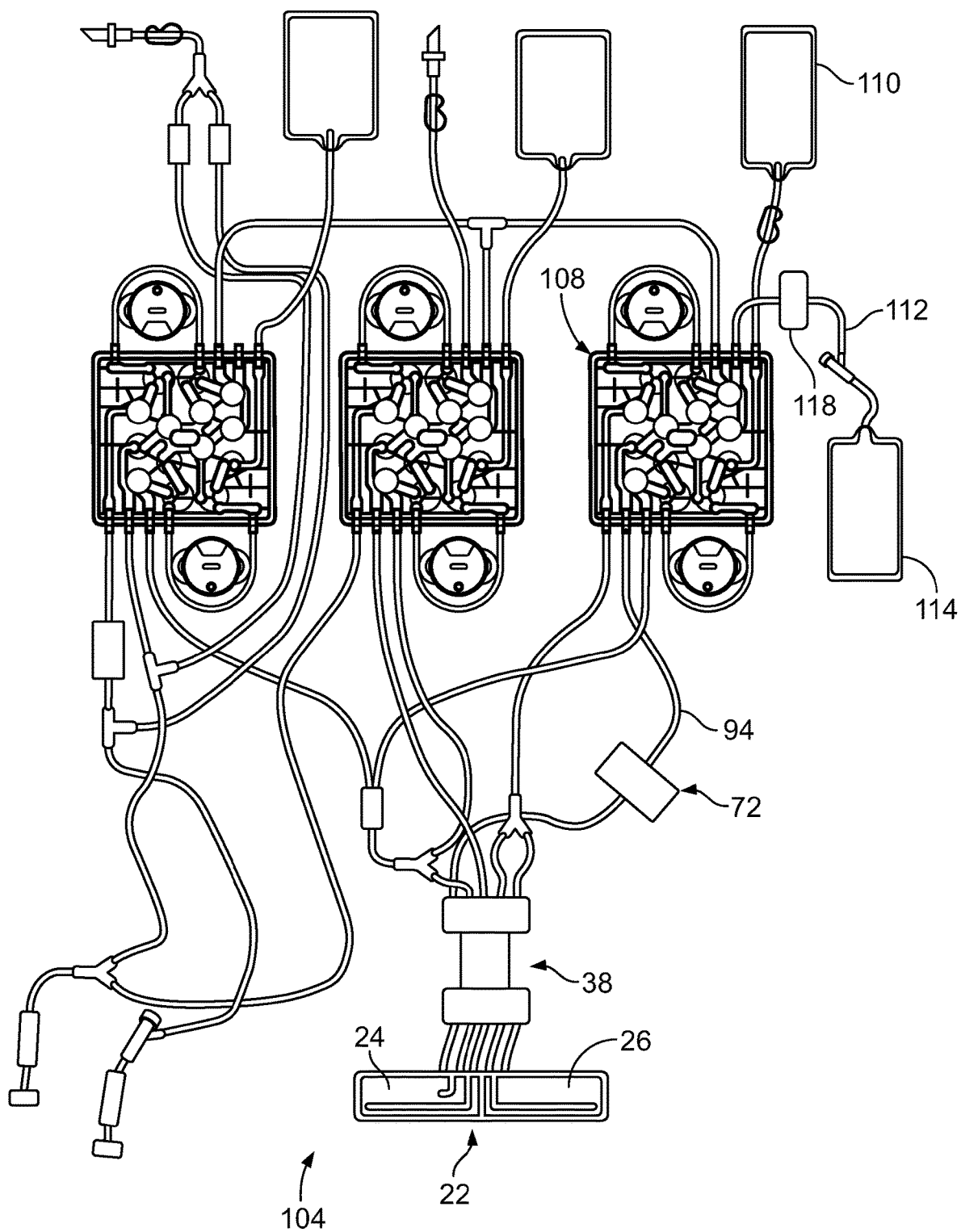
FIG. 13 is a front elevational view of an exemplary disposable fluid processing assembly that may be used in combination with the system of FIGS. 1 and 2 for carrying out blood separation procedures according to the present disclosure.

The blood separation chamber 22 can be variously constructed. FIG. 4 shows a representative embodiment, while FIG. 13 shows the blood separation chamber 22 in the context of a disposable fluid processing assembly that is used in combination with the system 10 to define a fluid flow path for blood, separated blood components, and other fluids (e.g., anticoagulant).

The chamber 22 shown in FIG. 4 allows for either single- or multi-stage processing. When used for multi-stage processing, a first stage 24 separates whole blood into first and second components. Depending on the nature of the separation procedure, one of the components may be transferred into a second stage 26 for further processing. When used for single-stage processing, only the first stage 24 is used for separating blood into its constituents, while the second stage 26 may be filled with saline or the like to balance the chamber 22.

Figure 3:
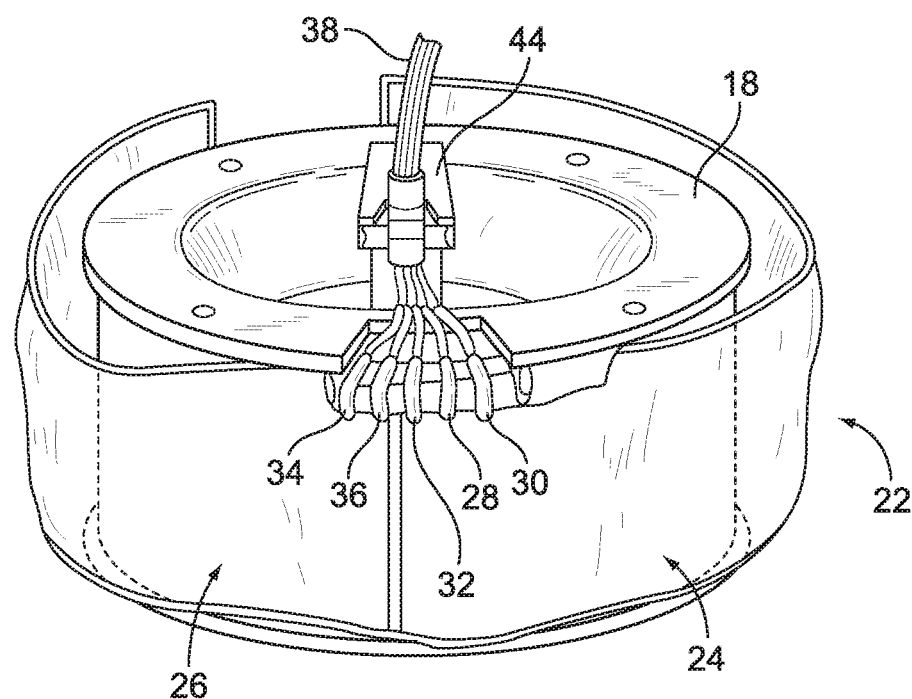
FIG. 3 is a top perspective view of the spool of the centrifuge shown in FIG. 2 in its upright position and carrying the blood separation chamber.

As FIGS. 3 and 4 best show, there are three ports 28, 30, and 32 associated with the first stage 24. Depending on the particular blood processing procedure, the ports may have different functionality but, in an MNC collection procedure, the port identified at 28 is used for conveying blood from a blood source or patient into the first stage 24. During such an MNC collection procedure, the other two ports 30 and 32 serve as outlet ports for separated blood components exiting the first stage 24. More particularly, the first outlet port 30 conveys a low density blood component from the first stage 24, while the second outlet port 32 conveys a high density blood component from the first stage 24.

In a method of carrying out single-stage processing, at least a portion of one or more of the separated components is returned to the blood source (which may be a living patient or donor or a non-living source, such as a fluid container), while at least a portion of at least one of the other separated components is removed from the first stage 24 and stored. For example, when carrying out an MNC collection procedure (as described in greater detail in U.S. Pat. No. 5,980,760, which is incorporated herein by reference), whole blood in the first stage 24 is separated into a plasma constituent (i.e., a low density component, which may include platelets), an interface or buffy coat or MNC-containing layer (i.e., an intermediate density component, which includes MNCs and may also include smaller red blood cells), and packed red blood cells (i.e., a high density component). The plasma constituent and packed red blood cells are removed from the first stage 24 (via the first and second outlet ports 30 and 32, respectively), while the MNC-containing layer builds up in the first stage 24. The plasma constituent may be returned to the blood source or collected, with at least a portion of the packed red blood cells being collected.

When the MNC-containing layer has built up to an adequate level within the first stage 24, the system 10 may transition to an MNC harvest phase. To harvest the MNCs in the MNC-containing layer, the second outlet port 32 may be closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection as an MNC product. If additional MNC product is to be collected, the alternating build-up and harvest phases may be repeated. When a sufficient amount of MNC product has been collected, the red blood cells may be either collected or returned to the blood source, or a portion of the red blood cells may be collected while another portion is returned to the blood source. Following collection, the MNC product may be treated to further processing (e.g., extracorporeal photopheresis, as discussed below).

In a different separation procedure, in which multi-stage processing is required, one of the separated blood components will be transferred from the first stage 24 to the second stage 26 via a port 34 associated with the second stage 26. The component transferred to the second stage 26 is further fractionated into sub-components, with one of the sub-components being removed from the second stage 26 via an outlet port 36 and the other sub-component remaining in the second stage 26. In the illustrated embodiment, the ports 28, 30, 32, 34, and 36 are arranged side-by-side along the top transverse edge of the chamber 22.

In one method of multi-stage operation, blood enters the first stage 24 via the port 28 and is separated into red blood cells (i.e., the high density blood component) and platelet-rich plasma (i.e., the low density blood component). The red blood cells are returned to the donor (via the port 32), while the platelet-rich plasma is conveyed out of the first stage 24 (via the first outlet port 30) and into the second stage 26 (via the inlet port 34). In the second stage 26, the platelet-rich plasma is separated into platelet-poor plasma and platelet concentrate. The platelet-poor plasma is removed from the second stage 26 (via the outlet port 36), leaving platelet concentrate in the second stage 26 for resuspension and transfer to one or more storage containers.

As best shown in FIG. 3, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 4 shows, a first interior seal 46 is located between the low density outlet port 30 and the inlet port 28. A second interior seal 48 is located between the inlet port 28 and the high density outlet port 32. The interior seals 46 and 48 form a fluid passage 50 (an inlet for whole blood or the like) and a low density collection region 52 in the first stage 24. The second seal 48 also forms a fluid passage 54 (a high density blood component outlet in an MNC collection procedure) in the first stage 24.

Figure 5:
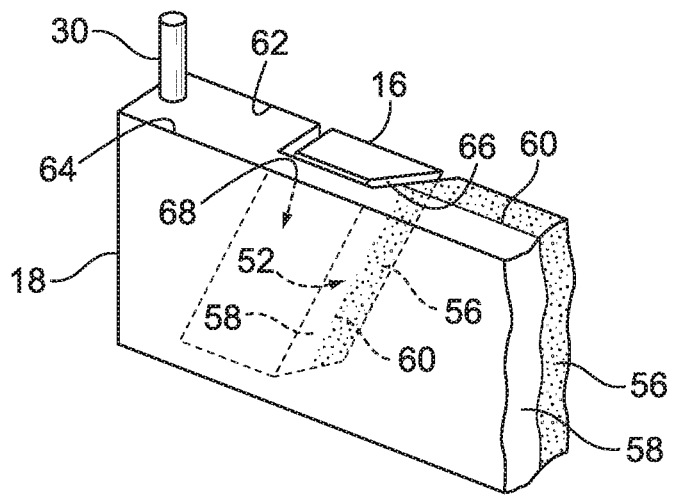
FIG. 5 is an enlarged perspective view of an interface ramp carried by the centrifuge in association with the blood separation chamber, showing the centrifugally separated red blood cell layer, plasma layer, and interface within the chamber when in a desired location on the ramp.

In an MNC collection procedure, the fluid passage 50 channels blood directly into the circumferential flow path immediately next to the low density collection region 52. As shown in FIG. 5, the blood separates into an optically dense layer 56 containing cellular components, which forms as cellular components move under the influence of centrifugal force toward the high-G (outer) wall 62. The optically dense layer 56 will include red blood cells (and, hence, will be referred to herein as the "RBC layer") but, depending on the speed at which the centrifuge 14 is spun, other cellular components (e.g., larger white blood cells and platelets) may also be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer or plasma constituent") but, depending on the speed at which the centrifuge 14 is rotated and the length of time that the blood is resident in the centrifuge, other components (e.g., smaller platelets) may also be present in the plasma layer 58.

The transition between the RBC layer 56 and the plasma layer 58 is generally referred to as the interface or buffy coat or MNC-containing layer 60, as described above and shown in FIG. 5. Platelets and white blood cells (including MNCs) typically occupy this transition region.

Figure 6:
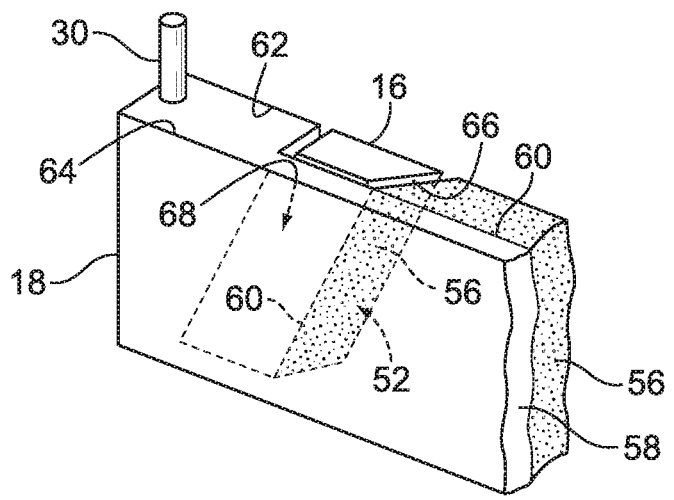
FIG. 6 is an enlarged perspective view of the interface ramp shown in FIG. 5, showing the red blood cell layer and interface at an undesired high location on the ramp.
Figure 7:
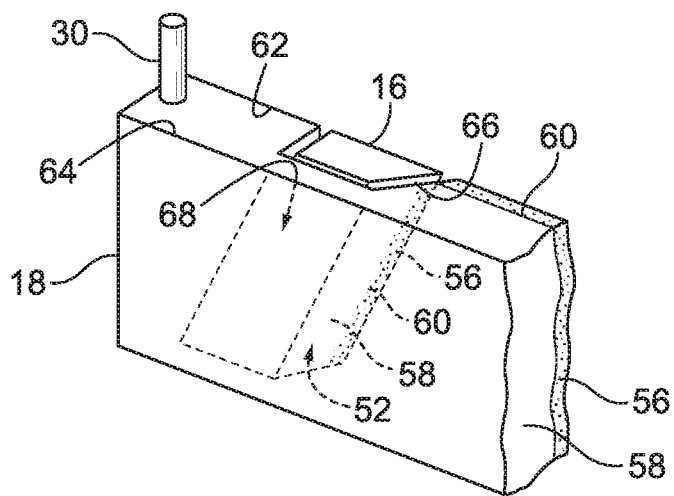
FIG. 7 is an enlarged perspective view of the interface ramp shown in FIG. 5, showing the red blood cell layer and interface at an undesired low location on the ramp.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), red blood cells can spill over and into the low density collection region 52, adversely affecting the quality of the plasma constituent 58. On the other hand, if the location of the interface 60 is too low (that is, if it resides too far away from the low-G wall 64, as FIG. 7 shows), the collection efficiency of the system 10 may be impaired.

As FIG. 5 shows, a ramp 66 extends from the high-G wall 62 of the bowl 16 at an angle across the low density collection region 52. The angle, measured with respect to the axis of the first outlet port 30 is about 30° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893 to Brown et al., which is incorporated herein by reference.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667, which is incorporated herein by reference.

C. The Interface Controller

The interface controller 12 (FIG. 11) includes a viewing head or interface optical sensor assembly 70 carried on the yoke 20 (see FIGS. 1 and 8) and an outlet optical sensor assembly 72 which is associated with tubing connected to the first outlet port 30. Alternatively, rather than being carried on the yoke 20, the interface optical sensor assembly 70 may be mounted to a radial location of the centrifuge bucket or enclosure, as described in U.S. Patent Application Publication Nos. 2014/0057771 and 2015/0219558, both of which are incorporated herein by reference. The interface optical sensor assembly 70 is oriented to optically view the transition in optical density between the RBC layer 56 and the plasma layer 58 on the ramp 66. The outlet optical sensor assembly 72 monitors the optical density of fluid exiting the first stage 24 via the first outlet port 30.

The interface controller 12 is functional to determine the location of the interface 60 on the ramp 66 and, if the interface 60 is located at an improper location (e.g., in the locations of FIG. 6 or 7), to correct the location of the interface 60.

(1) The Interface Optical Sensor Assembly

Figure 8:
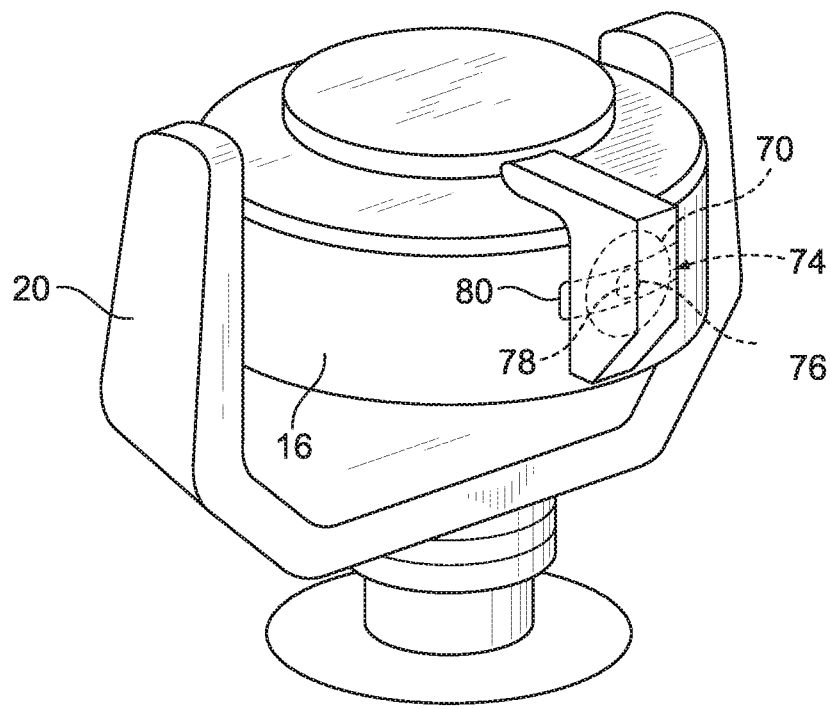
FIG. 8 is a side perspective view of the bowl and spool of the centrifuge when in the operating position, showing a viewing head, which forms a part of an interface controller, being carried by the centrifuge to view the interface ramp during rotation of the bowl.
Figure 9:
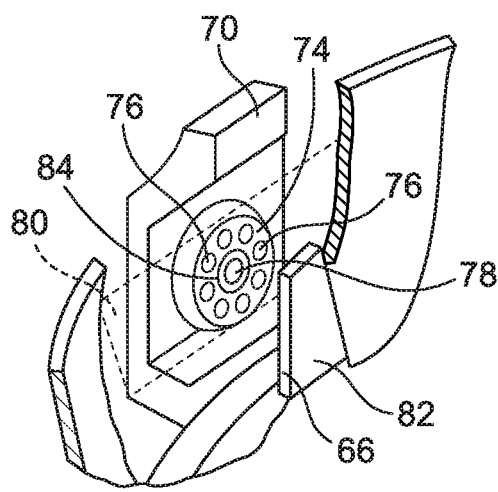
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
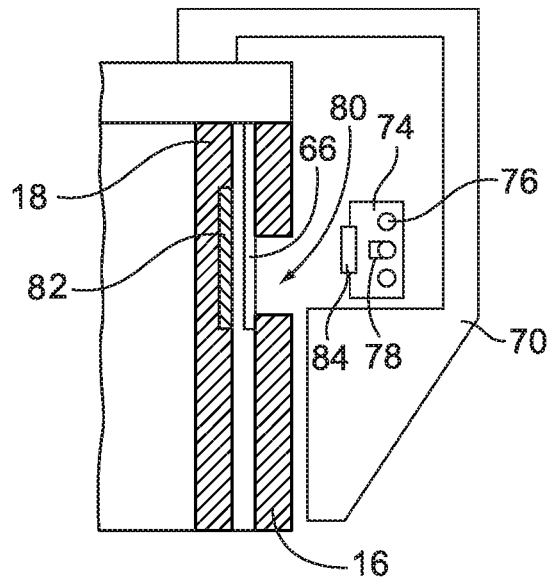
FIG. 10 is a side section view of the bowl, spool, and viewing head when the viewing head is aligned with the interface ramp.

Referring to FIGS. 8-10, the interface optical sensor assembly 70, carried by the yoke 20 or mounted to a stationary radial location of the centrifuge bucket or enclosure, includes a light source 74, which emits light that is absorbed by red blood cells. In the illustrated embodiment, the light source 74 includes a circular array of red light emitting diodes 76, but other wavelengths absorbed by red blood cells, like green or infrared, could also be used.

In the illustrated embodiment, seven light emitting diodes 76 comprise the light source 74. More diodes 76 may be used, or fewer diodes 76 can be used, depending upon the optical characteristics desired. Further, non-LED lights may also be employed without departing from the scope of the present disclosure.

The interface optical sensor assembly 70 also includes a light detector 78 (FIGS. 9 and 10), which is mounted adjacent to the light source 74. In one embodiment, the light detector 78 comprises a PIN diode detector, which is located generally in the geometric center of the circular array of light emitting diodes 76. Other types of light detectors may also be employed.

If mounted to the yoke 20, the yoke 20 and the interface optical sensor assembly 70 rotate at a one omega speed, as the spool 18 and bowl 16 rotate at an average speed of two omega. If mounted to a stationary portion of the centrifuge bucket or enclosure, the interface optical sensor assembly 70 remains stationary while the yoke 20 rotates at a one omega speed and the spool 18 and bowl 16 rotate at an average speed of two omega. The light source 74 directs light onto the rotating bowl 16. In the illustrated embodiment, the bowl 16 is transparent to the light emitted by the source 74 only in the region 80 where the bowl 16 overlies the interface ramp 66 (FIG. 8). In the illustrated embodiment, the region 80 comprises a window cut out in the bowl 16. The remainder of the bowl 16 that lies in the path of the interface optical sensor assembly 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and interface optical sensor assembly 70 align. The spool 18 may also carry a light reflective material 82 (FIGS. 9 and 10) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 9 and 10), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the interface optical sensor assembly 70, the detector 78 will first sense light reflected through the plasma layer 58 on the ramp 66. Eventually, the RBC layer 56 adjacent the interface 60 on the ramp 66 will enter the optical path of the interface optical sensor assembly 70. The RBC layer 56 absorbs light from the source 74 and thereby reduces the previously sensed intensity of the reflected light. The length of time that the higher intensity of reflected light is sensed by the detector 78 represents the amount of light from the source 74 that is not absorbed by the RBC layer 56 adjacent to the interface 60. With this information, a processing element or module 86 (FIG. 11) can determine the location of the interface 60 on the ramp 66 relative to the constricted passage 68. A more detailed discussion of the algorithms by which the interface controller 12 receives and processes signals to determine the location of the interface 60 on the ramp 66 may be found in U.S. Pat. No. 6,312,607 to Brown et al., which is incorporated herein by reference.

Figure 11:
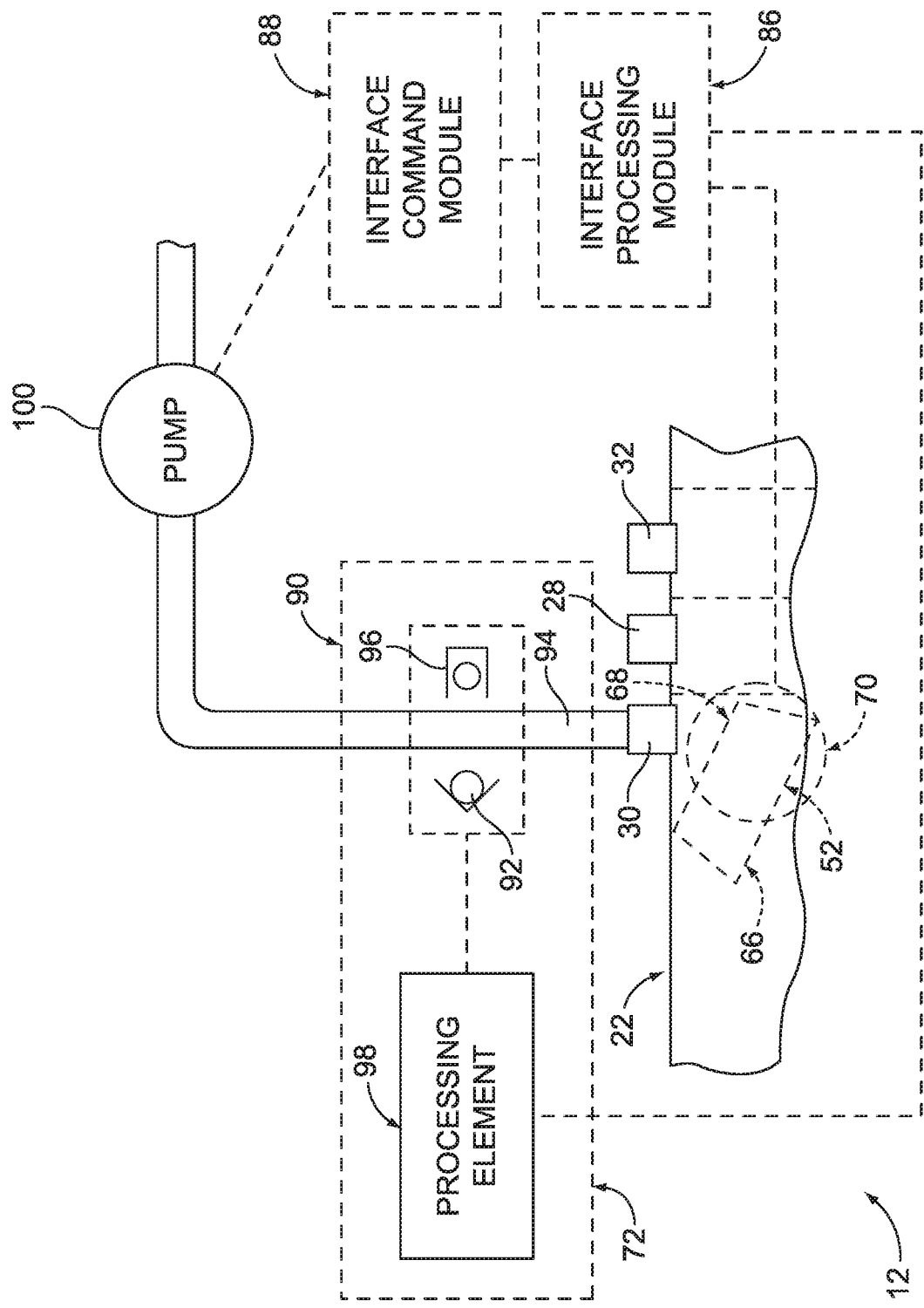
FIG. 11 is a schematic view of a blood calibration element, which forms a part of the interface controller.

When the location of the interface 60 on the ramp 66 has been determined, the processing element 86 outputs that information to an interface command element or module 88 (FIG. 11). The command element 88 includes a comparator, which compares the interface location output with a desired interface location to generate an error signal. The error signal may take a number of forms but, in one embodiment, is expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too small (as FIG. 7 shows). The interface command element 88 generates a signal to adjust an operational parameter accordingly, such as by increasing the rate at which plasma is removed through the first outlet port 30 under action of a pump 100 (FIG. 11). The interface 60 moves toward the constricted passage 68 to the desired control position (as FIG. 5 shows), where the error signal is zero.

A negative error signal indicates that the RBC layer 56 on the ramp 66 is too large (as FIG. 6 shows). The interface command element 88 generates a signal to adjust an operational parameter accordingly, such as by decreasing the rate at which plasma is removed through the first outlet port 30. The interface 60 moves away from the constricted passage 68 to the desired control position (FIG. 5), where the error signal is again zero.

(2) The Outlet Optical Sensor Assembly

The interface controller 12 further includes an outlet optical sensor assembly 72 (FIG. 11), which is configured to monitor the optical density of plasma outside of the blood separation chamber 22. The outlet optical sensor assembly 72 may be positioned anywhere in the fluid circuit outside of the blood separation chamber 22 where separated plasma is present but, in the illustrated embodiment is associated with tubing 94 connected to the first outlet port 30 so as to monitor plasma exiting the first stage 24. The outlet optical sensor assembly 72 compares the optical density of separated plasma to a baseline fluid (e.g., saline) exiting the first outlet port 30. If the optical density of the plasma is significantly different from saline (i.e., if the plasma has a reduced clarity), then it may be indicative of conditions of lipemia, hemolysis, or hyperbilirubinemia.

The outlet optical sensor assembly 72 includes an optical monitor 90 (see FIG. 11), which senses the optical density of fluid exiting the first outlet port 30 or (in the case of a multi-stage separation procedure) entering the second stage inlet port 34. In one embodiment, the optical monitor 90 is a conventional hemoglobin detector of the type used on the Autopheresis-C® blood processing device sold by Fenwal, Inc. The optical monitor 90 comprises a red light-emitting diode 92, which emits light into the outlet tubing 94 connected to the first outlet port 30 on the outside of the blood separation chamber 22. The optical monitor 90 further includes a PIN diode detector 96 on the opposite side of the tubing 94.

Different or additional light sources could also be used without departing from the scope of the present disclosure. For example, it may be advantageous to include separate red and green light-emitting diodes to distinguish between lipemic and hemolytic conditions in the whole blood and/or plasma layer 58. If, when considering plasma in the tubing 94, the overall transmissivity of the plasma is below a certain level (indicating that the plasma is relatively turbid and may be either lipemic or hemolytic), the red and green transmissions are separately considered. If the red and green transmissions decrease by a similar percentage (from the level of transmission through saline), then it is indicative of lipemia (because green and red light are absorbed to a similar extent by lipids). However, if the green transmission decreases to a much greater degree than the red transmission, it is indicative of hemolytic plasma (because green light is more readily absorbed by hemoglobin than red light).

The outlet optical sensor assembly 72 also includes a processing element 98, which receives signals from the monitor 90 to compute the optical transmission of the liquid conveyed through the tubing 94. A more detailed discussion of a set of exemplary algorithms by which the optical densities of the tubing 94 itself, saline present in the tubing 94, and plasma in the outlet tubing 94 may determined can be found in U.S. Pat. No. 6,312,607.

D. Dual-Sensor Pump and Contamination Detection Control

The optical density of the plasma layer 58 will vary according to the concentration of lipids, hemoglobin, and/or bilirubin in the plasma, which depends upon the physiology or morphology of the individual donor. Conditions of lipemia or hemolysis or hyperbilirubinemia or the like may decrease the optical density of the plasma to a level that differs significantly from saline or non-lipemic/hemolytic/hyperbilirubinemia plasma. As a result, the presence of plasma on the ramp 66 carrying high concentrations of lipids (lipemia) or hemoglobin (hemolysis) or bilirubin (hyperbilirubinemia) or the like diminishes the magnitude of the sensed voltage signals, independent of and unrelated to changes in the physical dimensions of the interface. Accordingly, the interface optical sensor assembly 70 may, in that situation, have reduced accuracy in monitoring the location of the interface 60 and any occurrence of plasma contamination.

As shown in FIG. 11, the processing element 98 of the outlet optical sensor assembly 72 is associated with the interface processing element or module 86, which is, in turn, associated with the interface command element or module 88. Accordingly, data collected and processed by the processing element 98 of the outlet optical sensor assembly 72 may be considered when determining the location of the interface 60 and/or taking corrective action to reposition the interface 60. In particular, the data collected by the outlet optical sensor assembly 72 may be employed for interface or contamination detection control as outlined in FIG. 12.

Figure 12A:
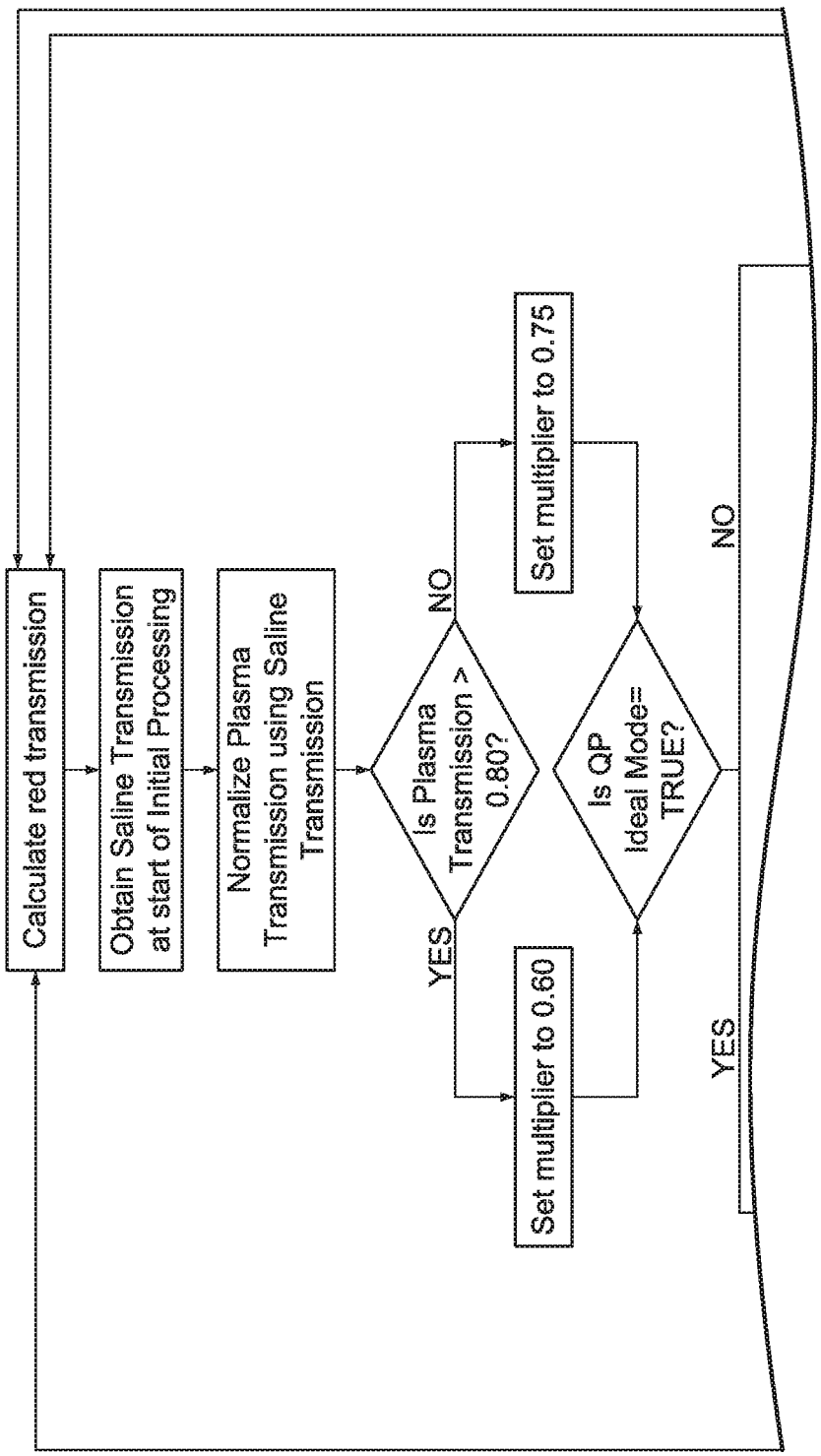
FIGS. 12A and 12B are first and second portions of a flowchart which shows the process undertaken by the interface controller when selecting the interface control mode.
Figure 12B:
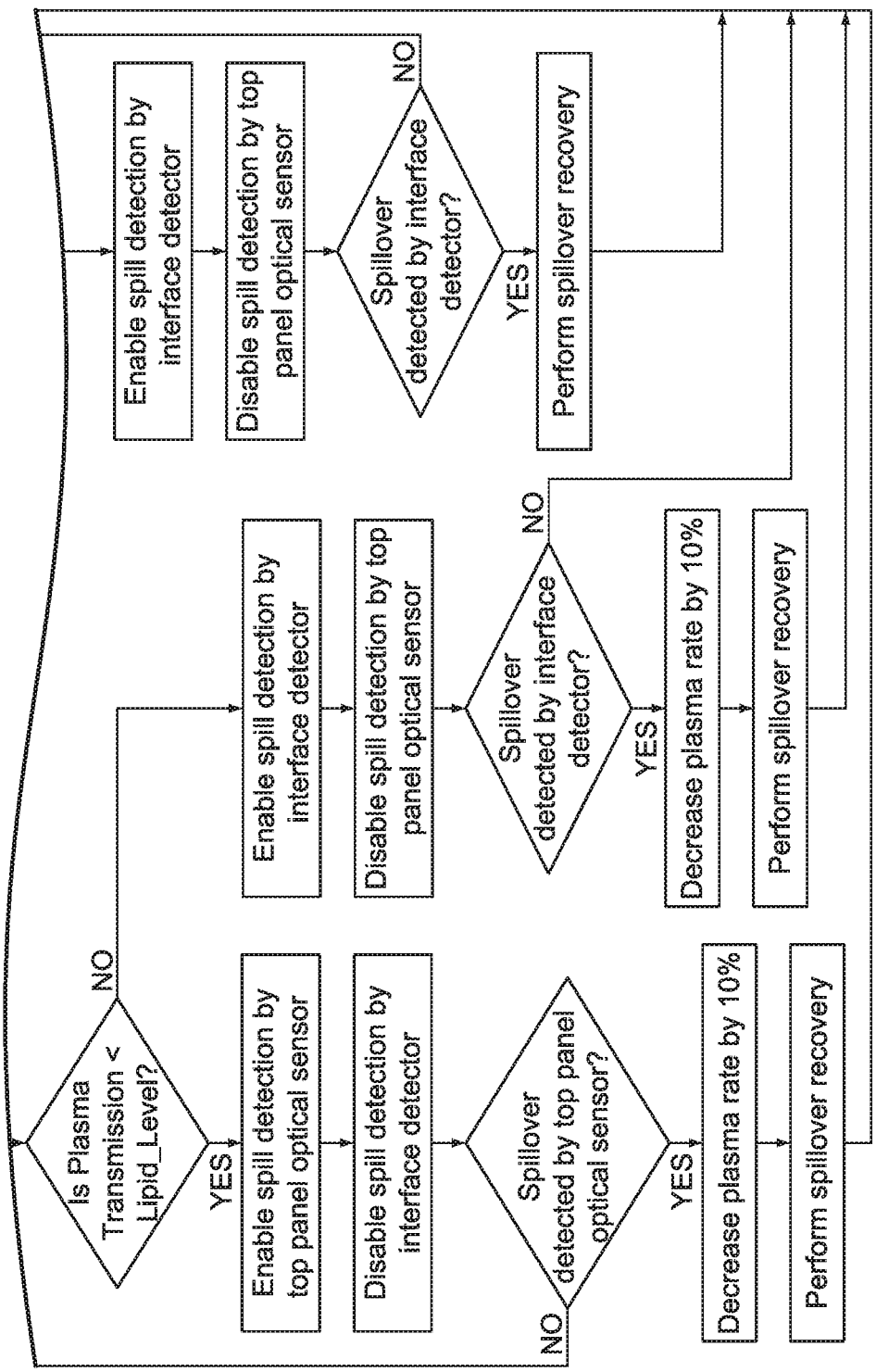

The control scheme outlined in FIGS. 12A and 12B includes two parts, a pump control module (illustrated generally in FIG. 12A) and a contamination detection module (illustrated generally in FIG. 12B), which may be employed together or individually. It may be preferred to employ the modules together, as the pump control module helps to improve the collection efficiency of the system, while the contamination detection module selects the most appropriate sensor assembly for monitoring separated plasma and preventing contamination thereof.

The control scheme outlined in FIGS. 12A and 12B will be described herein with reference to an outlet optical sensor assembly 72 having only a red light-emitting diode as a light source 92. Such a simplified outlet optical sensor assembly 72 can be used to identify plasma turbidity, but may not distinguish between conditions of lipemia, hemolysis, hyperbilirubinemia, and the like. In one embodiment, the same diagnostic and corrective steps are taken regardless of whether lipemic/hemolytic/hyperbilirubinemia/etc. conditions are present, so it is unnecessary to determine the exact cause of the plasma turbidity. However, a more advanced interface controller 12 (e.g., one with an outlet optical sensor assembly 72 capable of distinguishing between lipemic and hemolytic conditions) may also be employed without departing from the scope of the present disclosure. A more advanced interface controller 12 may be advantageous when employing a control scheme which takes different diagnostic and/or corrective steps depending on whether turbid plasma is lipemic or hemolytic or caused by some other irregularity, such as hyperbilirubinemia.

First, prior to fluid processing, the effect of the outlet tubing 94 on the transmission of light therethrough may be determined by the processing element 98 of the outlet optical sensor assembly 72. This may be achieved in any of a number of ways but, in one embodiment, involves taking a variety of measurements of the light which passes through and the light which does not pass through the empty outlet tubing 94. For example, these measurements may include: (1) the amount of light from the light source 92 which passes through the outlet tubing 94, (2) the amount of light from the light source 92 which does not pass through the outlet tubing 94, (3) the amount of background light which passes through the outlet tubing 94, and (4) the amount of background light which does not pass through the outlet tubing 94. Typically, measurements of the background light are taken while the light source 92 is turned off.

The amount of light from the light source 92 which passes through the outlet tubing 94 is subtracted from the amount of background light which passes through the outlet tubing 94 to arrive at a "corrected transmitted light" value. Similarly, the amount of light from the light source 92 which does not pass through the outlet tubing 94 is subtracted from the amount of background light which does not pass through the outlet tubing 94 to arrive at a "corrected non-transmitted light" value. The "corrected transmitted light" value may be divided by the "corrected non-transmitted light" value to arrive at a normalized value which accounts for the effect of the outlet tubing 94 on the transmission of light therethrough. This "correction factor" may be used to correct any future measurements taken during fluid processing.

With the "correction factor" so calculated, saline is then pumped into and through the system to prime the system. As the saline exits the first stage 24 via the first outlet port 30, the transmission of light from the light source 92 (red light in one embodiment) through the outlet tubing 94 is measured by the processing element 98. The "correction factor" may be applied to the measured value to arrive at a corrected or normalized measurement of the red light transmitted through the tubing 94 and saline. This process is represented in FIG. 12A by the box containing the words "Obtain Saline Transmission at start of Initial Processing."

When the system has been suitably primed, blood from a blood source is pumped into the first stage 24, where it is separated into a plasma layer 58 and an RBC layer 56, with an interface 60 therebetween. The plasma layer 58 is removed from the first stage 24 via the first outlet port 30 (under action of the pump 100), while the RBC layer 56 exits the first stage 24 via the second outlet port 32 and the interface 60 builds up in the first stage 24.

The outlet optical sensor assembly 72 monitors fluid flowing from the first outlet port 30 (which informs the system 10 when the plasma layer 58 flowing through the first outlet port 30 transitions to the interface 60 during MNC harvest), and periodically assesses the transmissivity of the fluid plasma layer 58 in the tubing 94 (i.e., the plasma layer 58 while building up the interface 60 in the first stage 24 and the interface 60 during MNC harvesting). As when determining the transmissivity of saline moving through the tubing 94, the processing element 98 of the outlet optical sensor assembly 72 may apply the "correction factor" to the measured value to arrive at a corrected or normalized measurement of the red light transmitted through the tubing 94 and the fluid flowing therethrough.

When the outlet optical sensor assembly 72 has determined both the transmissivity of light through the saline-filled tubing 94 and the transmissivity of light through the plasma- or interface-filled tubing 94, the plasma or interface transmission is normalized by dividing the plasma or interface transmissivity by the saline transmissivity. The higher the normalized transmission value is (up to a maximum value of 1.0, which indicates a plasma layer 58 or interface 60 as clear as saline), the clearer the plasma layer 58 or interface 60. The normalized transmission value is employed as an input or control factor for both the pump control module and the contamination detection module of the control scheme. This process, as carried out while building up the interface 60 in the first stage 24, is represented in FIG. 12A by the box containing the words "Normalize Plasma Transmission using Saline Transmission."

(1) Pump Control Module

The pump control module helps to improve the collection efficiency of the system by selecting the speed at which at least one of the pumps of the system operates based on the light transmissivity of a separated blood component. A specific implementation of a pump control module is illustrated in FIG. 12A, but the functionality of such a module can be generalized as follows. The system determines the light transmissivity of a separated blood component. The transmissivity is used as an input for calculating a weighted or adjusted flow rate, which is compared to the actual flow rate of the separated blood component. Whichever of the two flow rates is greater, the interface controller 12 will set the selected pump to operate at that flow rate.

Turning now to the specific implementation of the pump control module illustrated in FIG. 12A, during interface build-up, the normalized transmission value of the separated plasma is compared to a threshold value, which is an empirically determined value resulting in the desired control protocol. As such, the threshold value may vary depending on the nature of the separation hardware and the particular separation procedure being executed. This process is represented in FIG. 12A by the diamond containing the words "Is Plasma Transmission>0.80?"

When the normalized transmission value is greater than the threshold value (0.80 in one embodiment, which is indicative of relatively clear plasma), the processing element 98 sets a multiplier equal to a first value. This process is represented in FIG. 12A by the box containing the words "Set multiplier to 0.60."

When the normalized transmission value is less than 0.80 (indicating relatively cloudy plasma), the processing element instead sets the multiplier to a second value. This process is represented in FIG. 12A by the box containing the words "Set multiplier to 0.75." As will be described in greater detail below, the multiplier serves to bias the system toward selecting one of a number of possible pump control responses.

The actual first and second multiplier values may vary from system to system and are typically determined by empirical testing to arrive at values which result in the proper pump control response being initiated. However, in the illustrated embodiment, a first value of 0.60 is a suitable multiplier when the normalized transmission value is greater than 0.80 and a second value of 0.75 is a suitable multiplier when the normalized transmission value is less than 0.80.

The processing element 98 then multiplies an ideal plasma flow rate $Q_{IDEAL}$ by the multiplier to arrive at a calculated value $Q_{ADJUSTED}$. The ideal plasma flow rate $Q_{IDEAL}$ is a calculated value based on the hematocrit of the blood (which may be determined prior to processing by known methods) and represents a theoretical plasma flow rate at which the interface is properly positioned within the system for optimal collection efficiency. In the illustrated system, the ideal plasma flow rate $Q_{IDEAL}$ is calculated using the following formula: $Q_{IDEAL}=Q_{WB}*(1-Hct_{WB}/Hct_{RBC})$, where $Q_{WB}$ is the flow rate of whole blood, $Hct_{WB}$ is the hematocrit of whole blood entering the system and $Hct_{RBC}$ is the hematocrit of the RBC layer 56 exiting the system. Other methods of calculating $Q_{IDEAL}$ may also be employed without departing from the scope of the present disclosure.

The calculated value $Q_{ADJUSTED}$ is compared to the actual plasma flow rate $Q_{ACTUAL}$ determined by the interface optical sensor assembly 70 (which may be determined by any of a number of methods). The plasma flow rate is then set (typically by directly adjusting the operational rate of the plasma pump 100, if provided) to whichever of the two values is greater. This process is represented in FIG. 12A by the box containing the words "Is QP Ideal Mode=TRUE?"

It will be seen that the multiplier and, hence, $Q_{ADJUSTED}$ will be relatively small when the normalized transmission is greater (because the multiplier is 0.60 in the illustrated example) and will be relatively large when the normalized transmission is lower (because the multiplier is 0.75 in the illustrated example). Thus, it is more likely that the plasma flow rate will be set to $Q_{ACTUAL}$ when the plasma is relatively clear (i.e., probably normal and neither lipemic nor hemolytic) and more likely that the plasma flow rate will be set to $Q_{ADJUSTED}$ when the plasma is relatively cloudy (i.e., possibly lipemic or hemolytic). When the plasma is relatively clear, it may be preferred to set the plasma flow rate at $Q_{ACTUAL}$ for improved plasma contamination prevention. Similarly, when the plasma is less clear, it may be preferred to set the plasma flow rate at $Q_{ADJUSTED}$ for improved plasma removal efficiency.

When the readings from the interface optical sensor assembly 70 are reliable (i.e., when it is not "blinded" by the presence of excessive lipids or the like), the plasma flow rate may be controlled as a proportional-integral-derivative ("PID") control system, which works to minimize the difference between the commanded position of the interface 60 on the ramp 66 and the actual position of the interface 60 on the ramp 66. The PID control system considers the present difference between the two interface positions ("the P term"), differences between the two interface positions in the past ("the I term"), and a prediction of future differences between the two interface positions ("the D term"). As described above, when the interface optical sensor assembly 70 can no longer be relied upon (e.g., due to the presence of excessive lipids or the like, causing the interface 60 to appear to be located above the proper position), responsibility for spillover detection and prevention is handed over to the outlet optical sensor assembly 72. During this time, the outlet optical sensor assembly 72 may reduce the plasma flow rate to prevent or respond to a spillover condition, as described above, rather than functioning in the PID control mode.

When appropriate (i.e., when it has been determined that the readings from the interface optical sensor assembly 70 may be relied upon), spillover detection and prevention responsibilities may be passed back to the interface optical sensor assembly 70. The interface optical sensor assembly 70 may remain operational (albeit, without spillover detection and prevention responsibilities) the entire time that the outlet optical sensor assembly 72 has spillover detection and prevention responsibilities, in which case it is possible for the I term of the PID control system to increase. A large I term decreases the speed at which the PID control system will operate to increase the plasma flow rate to the appropriate level, so it may be advantageous for the controller 12 to reset the I term to zero when handing spillover detection and prevention responsibilities back to the interface optical sensor assembly 70. By working with an I term that is equal to zero, the responsiveness of the PID control system is increased, thereby increasing the plasma flow rate to the proper level more quickly than if the I term were to remain unchanged at the time that spillover detection and prevention responsibilities are returned to the interface optical sensor assembly 70. After resetting the I term, the I term may be allowed to increment or decrement on its own (i.e., without interference or influence from the controller 12) while the interface optical sensor assembly 70 has spillover detection and prevention responsibility for improved ongoing control and adjustment of the plasma flow rate in the PID control mode.

Thus, by the foregoing control scheme, the transmissivity of the plasma may be used to select the plasma flow rate.

(2) Contamination Detection Module

The contamination detection module helps to select the most appropriate sensor assembly for monitoring separated plasma and preventing contamination thereof. A specific implementation of a contamination detection module is illustrated in FIG. 12B, but the functionality of such a module can be generalized as follows. The system determines the light transmissivity of a separated blood component. The transmissivity (or a value based at least in part upon the transmissivity) is used as a basis for selecting which of a number of contamination detectors to use and the contamination prevention steps to be carried out by the interface controller 12.

The contamination detection module may be employed separately from the pump control module. For example, if the pump control module is omitted, the transmissivity of the separated blood component may be determined and normalized (e.g., as described above in reference to operation of the pump control module and as illustrated in FIG. 12A by the boxes containing the words "Calculate red transmission" and "Normalize Plasma Transmission using Saline Transmission"). If the normalized transmission value is greater than a particular level, the separated blood component is considered "relatively clear" and certain steps are performed (as described in greater detail below). If the normalized transmission value is less than the selected level, the separated blood component is considered "relatively cloudy" and different steps are performed (as described in greater detail below).

However, while the contamination detection module may be employed independently, it may be advantageous for the contamination detection module to be executed following the pump control module (as illustrated by the arrows extending from FIG. 12A to FIG. 12B) for improved plasma collection efficiency. When both modules are employed, the normalized transmission value may be used as an input to the contamination detection module, similar to when the pump control module is omitted. Alternatively, the output of the pump control module (which is based in part on the transmissivity of the separated blood component) may be employed to designate whether the separated blood component is "relatively clear" or "relatively cloudy." In one preferred embodiment (employing the pump control module of FIG. 12A), if the plasma flow rate is set to $Q_{ACTUAL}$ by the pump control module (as described above), then it is an indication that the plasma is "relatively clear" (i.e., conditions of lipemia, hemolysis, hyperbilirubinemia, and the like are not present, with a sufficiently high normalized transmission value). On the other hand, if the plasma flow rate is set to $Q_{ADJUSTED}$ by the pump control module (as described above), then it is an indication that the plasma is "relatively cloudy" (i.e., conditions of lipemia, hemolysis, hyperbilirubinemia, or the like may be present).

(a) Relatively Clear Plasma

When it is determined that the plasma is "relatively clear" (per the foregoing criteria or any other suitable criteria), it is safe for the interface controller 12 to select the interface optical sensor assembly 70 for contamination detection duty (i.e., monitoring the separated plasma for the presence of cellular components or for a transition from plasma flow to interface flow). This process is represented in FIG. 12B by the rightmost box containing the words "Enable spill detection by interface detector." When the interface optical sensor assembly 70 has been selected for further process monitoring, the outlet optical sensor assembly 72 is disabled of its contamination detection functionality. This process is represented in FIG. 12B by the rightmost box containing the words "Disable spill detection by top panel optical sensor."

When it has been selected for further process monitoring, the interface optical sensor assembly 70 operates to determine whether the separated plasma has been contaminated by a spillover (i.e., by cellular blood components spilling into the plasma outlet line). This process is represented in FIG. 12B by the rightmost diamond containing the words "Spillover detected by interface detector?" Many methods of optically detecting plasma contamination are in practice today and known to those of ordinary skill in the art and any of these methods (or methods yet to be practiced) may be employed without departing from the scope of the present disclosure.

If the interface optical sensor assembly 70 finds there to be no contamination of the plasma, then the control system returns to its initial step and the process repeats itself. This is represented in FIGS. 12A and 12B by the "NO" arrow leading from the rightmost diamond containing the words "Spillover detected by interface detector?" (FIG. 12B) to the box containing the words "Calculate red transmission" (FIG. 12A).

If the interface optical sensor assembly 70 detects contamination of the plasma, then the control system takes steps to counteract the contamination. This is represented in FIG. 12B by the rightmost box containing the words "Perform spillover recovery." Many methods of counteracting plasma contamination are in practice today and known to those of ordinary skill in the art and any of these methods (or methods yet to be practiced) may be employed without departing from the scope of the present disclosure. For example, the system may respond to a spill by reversing the flow in the outlet line 94 until the spill clears. In another embodiment, the operation of the plasma pump 100 is slowed and the outflowing plasma is temporarily diverted from a collection container to the donor or patient until the spill clears, at which time collection of the plasma may resume. When the anti-contamination steps have been carried out, the control system returns to its initial step and the process repeats itself. This is represented in FIGS. 12A and 12B by the arrow leading from the rightmost box containing the words "Perform spillover recovery" (FIG. 12B) to the box containing the words "Calculate red transmission" (FIG. 12A).

(b) Relatively Cloudy Plasma

On the other hand, if it is determined that the plasma is "relatively cloudy" (per the foregoing criteria or any other suitable criteria), then another calculation is made prior to selecting the appropriate sensor assembly for further process monitoring. This process is represented in FIG. 12B by the diamond containing the words "Is Plasma Transmission <Lipid_Level?"

In particular, the normalized plasma transmission value is compared to a "Lipid_Level" value, which is indicative of the presence of excess lipids or hemoglobin or bilirubin or the like in the plasma layer 58. This value may vary from system to system and is typically determined by empirical testing to arrive at a value which results in the proper optical sensor assembly being selected for further process monitoring. However, in one embodiment, a "Lipid_Level" value of 0.7 is selected to compare against the normalized plasma transmission value.

(i) Normalized Plasma Transmission Value Greater than Lipid_Level Value

If the normalized plasma transmission value is greater than 0.7 (or whatever the "Lipid_Level" value may be), then it is an indication that the plasma layer 58, while being relatively cloudy, is subject to only slight conditions of lipemia or hemolysis or hyperbilirubinemia or the like, in which case it is acceptable for the interface controller 12 to select the interface optical sensor assembly 70 to serve as the interface detector. This process is represented in FIG. 12B by the leftmost box containing the words "Enable spill detection by interface detector" (i.e., at the end of the "NO" arrow leading from the diamond containing the words "Is Plasma Transmission <Lipid_Level?"). When the interface optical sensor assembly 70 has been selected for further process monitoring, the outlet optical sensor assembly 72 is disabled of its contamination detection functionality. This process is represented in FIG. 12B by the leftmost box containing the words "Disable spill detection by top panel optical sensor."

When it has been selected for further process monitoring, the interface optical sensor assembly 70 operates to determine whether the separated plasma has been contaminated by cellular blood components spilling into the plasma. This process is represented in FIG. 12B by the leftmost diamond containing the words "Spillover detected by interface detector?" Many methods of optically detecting plasma contamination are in practice today and known to those of ordinary skill in the art and any of these methods (or methods yet to be practiced) may be employed without departing from the scope of the present disclosure.

If the interface optical sensor assembly 70 finds there to be no contamination of the plasma, then the control system returns to its initial step and the process repeats itself. This is represented in FIGS. 12A and 12B by the "NO" arrow leading from the leftmost diamond containing the words "Spillover detected by interface detector?" (FIG. 12B) to the box containing the words "Calculate red transmission" (FIG. 12A).

If the interface optical sensor assembly 70 detects contamination of the plasma, then the control system takes steps to counteract the contamination. In the illustrated embodiment, this is represented in FIG. 12B by the rightmost box containing the words "Decrease plasma rate by 10%" and the center box containing the words "Perform spillover recovery."

If the control system is performing the "relatively cloudy plasma" routine and contamination of the plasma layer 58 is detected, it is an indication that the interface 60 may be closer to the low-G wall 64 than it should be. Thus, it may be desirable to decrease the plasma rate by some factor to increase the height of the plasma layer 58 on the ramp 66, which has the effect of moving the interface 60 away from the low-G wall 64. In the illustrated embodiment, the plasma rate is decreased by 10%, but it may also be decreased by some other factor without departing from the scope of the present disclosure.

As for the spillover recovery steps performed by the system, many methods of counteracting plasma contamination (e.g., by attempting to draw plasma from the outlet line 94 back into the first stage 24) are in practice today and known to those of ordinary skill in the art and any of these methods (or methods yet to be practiced) may be employed without departing from the scope of the present disclosure.

When the anti-contamination steps have been carried out, the control system returns to its initial step and the process repeats itself. This is represented in FIGS. 12A and 12B by the arrow leading from the center box containing the words "Perform spillover recovery" (FIG. 12B) to the box containing the words "Calculate red transmission" (FIG. 12A).

(ii) Normalized Plasma Transmission Value Less than Lipid_Level Value

If the normalized value is less than 0.7 (or whatever the "Lipid_Level" value may be), then it is an indication that the cloudiness of the plasma layer 58 is due to conditions of lipemia or hemolysis or hyperbilirubinemia or the like, and that the interface optical sensor assembly 70 is not suitable for properly monitoring the location of the interface 60 and preventing plasma contamination. In this case, the outlet optical sensor assembly 72 is selected as the interface detector. This process is represented in FIG. 12B by the box containing the words "Enable spill detection by top panel optical sensor" (i.e., at the end of the "YES" arrow leading from the diamond containing the words "Is Plasma Transmission<Lipid_Level?"). When the outlet optical sensor assembly 72 has been selected for further process monitoring, the interface optical sensor assembly 70 is disabled of its contamination detection functionality. This process is represented in FIG. 12B by the box containing the words "Disable spill detection by interface detector."

In general, it may be preferred to use the interface optical sensor assembly 70 instead of the outlet optical sensor assembly 72 for contamination detection (e.g., because the interface optical sensor assembly 70 is located further upstream in the system and may be better suited to avoiding plasma contamination). However, as described above, if conditions of lipemia or hemolysis or hyperbilirubinemia or the like are present at a sufficiently high level, conventional interface control means are unsuitable and the automated control system of the present invention is preferred to known systems, which must resort to manual inspection and intervention when processing plasma of decreased clarity.

When the outlet optical sensor assembly 72 has been chosen for further process monitoring, it operates to determine whether the separated plasma has been contaminated by cellular blood components spilling into the plasma. This process is represented in FIG. 12B by the diamond containing the words "Spillover detected by top panel optical sensor?" The outlet optical sensor assembly 72 compares the transmissivity of the plasma layer 58 to a minimum transmission value which is indicative of contamination of the plasma layer 58. When the plasma layer 58 is contaminated, the outlet optical sensor assembly 72 will be "blinded" by cellular components, thereby drastically reducing the normalized plasma transmission value. For example, in one embodiment, the outlet optical sensor assembly 72 will only register contamination upon a normalized transmission value less than 0.1, which is much lower than the normalized transmission value of even highly cloudy plasma.

If the normalized transmission value is greater than or equal to 0.1 (i.e., that the plasma has a sufficiently low clarity without being contaminated by cellular blood components), then the control system returns to its initial step and the process repeats itself. This is represented in FIGS. 12A and 12B by the "NO" arrow leading from the leftmost diamond containing the words "Spillover detected by top panel optical sensor?" (FIG. 12B) to the box containing the words "Calculate red transmission" (FIG. 12A).

On the other hand, if the normalized transmission value is less than 0.1, it is an indication that the plasma layer 58 has been contaminated. Various steps may be taken to respond to contamination but, in the illustrated embodiment, the interface command element 88 responds by decreasing the plasma flow rate (e.g., by 10% in the illustrated embodiment) and then initializing a "perform spillover recovery" step. These steps are illustrated in FIG. 12B by the leftmost box containing the words "Decrease plasma rate by 10%" and the leftmost box containing the words "Perform spillover recovery." The purpose of decreasing the plasma rate is to move the interface 60 away from the low-G wall 64, thereby decreasing the likelihood of future contamination.

The anti-contamination steps carried out by the interface command element 88 may be either the same as those performed in the event of plasma contamination when the normalized transmission value is greater than the "Lipid_Level" value or different. When the anti-contamination steps have been carried out, the control system returns to its initial step and the process repeats itself. This is represented in FIGS. 12A and 12B by the arrow leading from the leftmost box containing the words "Perform spillover recovery" (FIG. 12B) to the box containing the words "Calculate red transmission" (FIG. 12A).

(3) Subsequent Iterations

The step of checking the saline transmissivity (i.e., the step represented in FIG. 12A by the box containing the words "Obtain Saline Transmission at start of Initial Processing") may be avoided or eliminated once a subsequent iteration of the control process begins, as the same saline transmissivity value which is initially determined may be used for the entire procedure.

The control process of FIGS. 12A and 12B may be repeated periodically, for example, once every second. If the process repeatedly finds that the separated plasma is sufficiently cloudy or turbid (e.g., with a normalized plasma transmission value less than 0.80), but not contaminated (e.g., registering a normalized plasma transmission value greater than or equal to 0.1), then the system may trigger an alarm or indicator which signifies conditions of lipemia or hemolysis or hyperbilirubinemia or the like. In one embodiment, this alarm or indicator is only triggered once and only if the normalized transmission value falls within the aforementioned range for five consecutive seconds.

(4) Conflicting Contamination Readings

It is possible for the readings from the interface and outlet optical sensor assemblies 70 and 72 to conflict, with the interface optical sensor assembly 70 detecting a spillover condition while the outlet optical sensor assembly 72 indicates that the separated plasma is sufficiently clear. This may happen for any of a number of reasons, for example, due to the presence of cold agglutinins. As described above, detection of a spillover condition may cause a temporary decrease in the plasma flow rate through the outlet tubing 94 in order to move the interface to the proper position on the interface ramp 66, which is indicative of the spillover condition having been eliminated. However, if the outlet optical sensor assembly shows that the plasma is sufficiently clear, then reducing the plasma flow rate may not be the appropriate response, as the slowed plasma flow rate may only lengthen the procedure without correcting an actual spillover.

There are several ways to address the foregoing situation. In each case, the first step is determining whether there is a legitimate conflict between the interface and outlet optical sensor assemblies 70 and 72. The controller 12 or one or more components thereof (e.g., the processing element 98) may be programmed to consider the turbidity of the separated plasma in the outlet line 94 (which is determined using the outlet optical sensor assembly 72, as described above) and the number of times that the interface optical sensor assembly 70 has detected a spillover condition during a single procedure. If the separated plasma is determined to have a clarity greater than or equal to a predetermined or preselected level and the interface optical sensor assembly 70 has detected a spillover condition at least a predetermined or preselected number of times, then it is indicative of a conflict between the readings of the interface and outlet optical sensor assemblies 70 and 72.

In one embodiment, the plasma clarity level is chosen as being a minimum value at which the plasma is considered to be non-turbid, while the number of spillover condition detections is chosen to be three. In other embodiments, the plasma clarity level and/or the number of spillover condition detections may be different. For example, it may be advantageous to select a higher plasma clarity level to better ensure that the separated plasma in the outlet line 94 is not turbid. As for the number of spillover condition detections, it may be advantageous for a greater number to be selected to better ensure that a conflict between the interface and outlet optical sensor assemblies 70 and 72 actually exists due to the nature of the separated plasma and that it is appropriate to carry out the following conflict resolution protocol. Conversely, there are also advantages in selecting a relatively low number (which may be lowered to detection of a single spillover condition) to improve separation efficiency by limiting the amount of time that the separated plasma is passed through the outlet line 94 at a reduced rate.

Upon a conflict being recognized, the interface optical sensor assembly 70 will be rendered temporarily incapable of triggering or initiating an anti-spillover response, for example, by preventing it from generating an output that causes the controller 12 to initiate a spillover countermeasure (such as reduction in or reversal of plasma flow rate) or by allowing the controller 12 to refuse to initiate a spillover countermeasure upon receiving the output from the interface optical sensor assembly 70. However, even though the interface optical sensor assembly 70 temporarily loses the ability to trigger an anti-spillover response, it may otherwise remain operational and continue monitoring the interface ramp 66. With the interface optical sensor assembly 70 so limited in its functionality, any one of a number of possible conflict resolution protocols may be initiated to continue the procedure.

According to a first conflict resolution protocol (which may be referred to as the "manual monitoring" approach), the system 10 alerts the operator of the conflict by an "excessive spillover condition" alert or alarm or notification. The system 10 may then inform the operator that, if they wish to continue the procedure, the operator should visually monitor the outlet line 94 for a spillover condition (i.e., plasma redness and/or turbidity). The outlet optical sensor assembly 72 may retain its ability to generate a signal or output to the controller 12 that triggers or initiates an anti-spillover response (e.g., reversing the direction of plasma flow through the outlet line 94 or decreasing the plasma flow rate) as a backup to the visual monitoring by the operator. Alternatively, both optical sensor assemblies 70 and 72 may temporarily lose their ability to trigger an anti-spillover response, with the operator having sole responsibility for spillover detection.

If the operator agrees to continue the procedure, then the controller 12 may do so, with the plasma flow rate either being returned to its most recent level (i.e., the plasma flow rate at the time of the "excessive spillover condition" alert or alarm or notification) or to some other rate. In particular, it may be advantageous to increase the plasma flow rate to a level greater than the rate at the time of the "excessive spillover condition" alert or alarm or notification for improved process efficiency. In one embodiment, the controller 12 may restore the plasma flow rate to the rate prior to the first spillover condition being detected, but the plasma flow rate may also be set to any other level without departing from the scope of the present disclosure.

If the operator observes a spillover condition in the outlet line 94, then they may inform the controller 12 (using a touchscreen or other user interface of the system 10), with the controller 12 responding in any of a number of ways (e.g., reversing the direction of plasma flow through the outlet line 94 or decreasing the plasma flow rate) or the operator may instruct the system 10 to end the procedure. It is also within the scope of the present disclosure for the operator to be given the ability to switch to a different conflict resolution protocol (e.g., if they lose confidence in their ability to detect a spillover condition or if they want additional control of the procedure).

According to an alternative conflict resolution protocol (which is a variation of the "manual monitoring" approach and may be referred to as the "manual control" approach), the operator is given more freedom to control the procedure. In particular, the operator may be given the ability to selectively increment the plasma flow rate after the procedure has been continued. It may be advantageous to set limits on the way in which the operator may increase the plasma flow rate (e.g., by setting a maximum plasma flow rate and/or a limit on the size of each increment and/or a limit on how frequent an increment may be ordered) to decrease the likelihood of a spillover condition or to ensure that the interface is not disrupted by a sudden, large increase in the plasma flow rate. The operator may have the ability to make other changes to the procedure as well (e.g., decreasing the whole blood draw rate) to address or avoid a spillover condition. It is also within the scope of the present disclosure for the operator to be given the ability to switch to a different conflict resolution protocol (e.g., if they lose confidence in their ability to detect a spillover condition).

According to another alternative conflict resolution protocol (which may be referred to as the "fully automated" approach), operator intervention may be eliminated entirely. In particular, the controller 12 may continue the procedure while automatically incrementing the plasma flow rate. The maximum level to which the plasma flow rate may be increased may be limited, such as by setting the maximum level to be a fraction of the ideal plasma flow rate (e.g., 95%), but it is also within the scope of the present disclosure to allow the controller 12 to increment the plasma flow rate until the ideal plasma flow rate is reached. It may be advantageous to limit the increase in flow rate resulting from each increment and/or the number of increments that may be ordered over a particular period of time (e.g., allowing only one increment per minute).

The outlet optical sensor assembly 72 continues monitoring the outlet line 94 and retains its ability to trigger an anti-spillover response (e.g., reversing the direction of plasma flow through the outlet line 94 or decreasing the plasma flow rate), and may cause the controller 12 to decrement the plasma flow rate should a spillover condition be detected by the outlet optical sensor assembly 72. Rather than setting a predetermined or preselected maximum level to which the plasma flow rate may be increased, it is within the scope of the present disclosure for the plasma flow rate to be automatically incremented until the outlet optical sensor assembly 72 detects a spillover condition, with the plasma flow rate being thereafter decremented to the extent necessary to continue the procedure without further spillover conditions being detected.

(5) Alternative Approach to Assessing Separated Plasma Clarity

According to another aspect of the present disclosure, a different approach may be employed to assessing the clarity of the separated plasma. For example, rather than relying upon the optical density of the separated plasma flowing out of the first stage 24 via the first outlet port 30, the current plasma flow rate (which may be set by the interface controller 12 of the system controller, as described above, or arrived at in some other way) may be compared to the calculated ideal plasma flow rate $Q_{IDEAL}$ by the interface controller 12 to assess plasma clarity. The current plasma flow rate will typically be different from the ideal plasma flow rate $Q_{IDEAL}$, and most typically lower than the ideal plasma flow rate $Q_{IDEAL}$. The percent difference or delta between the two flow rates is indicative of the clarity of the plasma. In particular, if the current plasma flow rate is significantly lower than the ideal plasma flow rate $Q_{IDEAL}$, then it is indicative of decreased plasma clarity, because otherwise the current plasma flow rate would be closer to the ideal plasma flow rate $Q_{IDEAL}$. Conversely, if the current plasma flow rate is not significantly lower than the ideal plasma flow rate $Q_{IDEAL}$, then it is indicative of acceptable plasma clarity.

The exact percent difference or delta or threshold value that separates "cloudy" from "clear" plasma may vary without departing from the scope of the present disclosure. In one embodiment, the percent difference or delta that separates "cloudy" from "clear" plasma may be in the range of approximately 25-30% (i.e., a current flow rate that is not within 25-30% of the ideal plasma flow rate $Q_{IDEAL}$ is indicative of decreased plasma clarity, while a current flow rate that is within approximately 25-30% of the ideal plasma flow rate $Q_{IDEAL}$ is indicative of acceptable plasma clarity). In another embodiment, the percent difference or delta that separates "cloudy" from "clear" plasma may be approximately 20% (i.e., a current flow rate that is less than or equal to 80% of the ideal plasma flow rate $Q_{IDEAL}$ is indicative of decreased plasma clarity, while a current flow rate that is more than 80% of the ideal plasma flow rate $Q_{IDEAL}$ is indicative of acceptable plasma clarity). "Cloudy" plasma tends to cause the plasma flow rate to decrease, so it may be preferred for the system controller to only consider the plasma to have decreased clarity if the current plasma flow rate is less than the ideal plasma flow rate $Q_{IDEAL}$ by a greater percent difference than the selected threshold value, rather than being greater than the ideal plasma flow rate $Q_{IDEAL}$ by a greater percent difference than the selected threshold value.

Determining that the separated plasma is "cloudy" or otherwise has decreased clarity may have any of a number of consequences, as outlined above. In one embodiment, if the current plasma flow rate is sufficiently low so as to be indicative of decreased plasma clarity, then the interface controller 12 or the operator may have the option of selectively increasing the plasma flow rate to a level between the current plasma flow rate and the ideal plasma flow rate $Q_{IDEAL}$. For example, if the current plasma flow rate is 15 ml/min (as selected by the PID control system described above, in one embodiment) and the ideal plasma flow rate $Q_{IDEAL}$ is 25 ml/min, the delta or percent difference is 40% (i.e., the current plasma flow rate is 60% of the ideal plasma flow rate $Q_{IDEAL}$), then that may be indicative of decreased plasma clarity under this approach. In such circumstances, either the interface controller 12 or the operator may be able to increase the plasma flow rate (to 22 ml/min, for example), as it is likely that the current plasma flow rate is unnecessarily low due to decreased plasma clarity (which may affect the determination of the location of the interface 60 on the interface ramp 66, as described above). The exact level to which the plasma flow rate is set and how long the new plasma flow rate is implemented (e.g., whether it is used as a default value during a subsequent cycle of a multi-cycle procedure) may vary without departing from the scope of the present disclosure.

If the operator is given the ability to increase the plasma flow rate, then it may be advantageous for the interface controller 12 to restrict the plasma flow rate that may be selected by the operator. For example, the interface controller 12 may prevent the operator from setting the plasma flow rate to a level that is greater than a particular percentage of the ideal plasma flow rate $Q_{IDEAL}$ or a level that is a certain percentage greater than the current plasma flow rate.

E. Mononuclear Cell Collection and Processing

The clarity of plasma may be of particular interest when collecting MNCs, especially when MNC collection is part of an extracorporeal photopheresis procedure. Extracorporeal photopheresis is a process that typically includes: (1) separation and collection of MNCs from other constituents of blood from a source, (2) photoactivation treatment of the collected MNCs, and (3) reinfusion of the treated MNCs back to the source. More specifically, extracorporeal photopheresis typically involves the extracorporeal exposure of separated MNCs combined with a photoactive compound, such as 8-methoxypsoralen or "8-MOP," which is then photoactivated or irradiated by a dosage of light of a particular wavelength (e.g., ultraviolet light). It is believed that the combination of 8-MOP and the dosage of light causes apoptosis or programmed cell death of the treated T-cells. Additionally, it has also been theorized that extracorporeal photopheresis also induces monocytes to differentiate into dendritic cells capable of phagocytosing and processing the apoptotic T-cell antigens. When these activated dendritic cells are re-infused into systemic circulation, they may cause a systemic cytotoxic CD8+ T-lymphocyte-mediated immune response to the processed apoptotic T-cell antigens. It will be appreciated that other possible mechanisms of action may be involved in achieving the benefits that have been observed from the extracorporeal photopheresis treatment of mononuclear cells and the subsequent benefits to patients undergoing extracorporeal photopheresis-based therapies. One conventional approach to extracorporeal photopheresis is described in U.S. Pat. No. 5,984,887, which is incorporated herein by reference.

(1) Adjusting Dosage of Irradiating Light

Certain types of light may be absorbed at higher levels by plasma if the plasma is cloudy or otherwise has decreased clarity. For example, ultraviolet light (which is commonly used to irradiate MNCs during extracorporeal photopheresis) is readily absorbed by lipids, which may be one cause of decreased plasma clarity. The separated MNCs are suspended in an amount of plasma, so the tendency of the plasma to absorb the irradiating light to an irregular degree affects the efficiency of the extracorporeal photopheresis procedure.

Accordingly, as part of an extracorporeal photopheresis procedure, the system controller may determine whether the separated plasma constituent has decreased clarity. The system controller may use any suitable approach to assessing plasma clarity, including the approaches described herein (i.e., assessing the light transmissivity of the plasma or comparing the current plasma flow rate to a calculated ideal plasma flow rate $Q_{IDEAL}$). If the system controller determines that the plasma does not have decreased clarity, then it may control an irradiation device (which may include communicating with the controller of a separate irradiation device) to subject the MNCs to a default dosage of light. On the other hand, if the system controller determines that the plasma does have decreased clarity, then it may control the irradiation device to subject the MNCs to a dosage of light that is greater than the default dosage (in duration and/or intensity). The exact dosage that is ordered by the system controller may depend on the clarity of the plasma. For example, when the plasma has a greatly reduced clarity, then the system controller may order a greater dosage of light than what would be ordered when the clarity of the plasma is decreased to a lesser degree.

The system controller may also use the clarity of the plasma constituent as a factor in adjusting other aspects of an extracorporeal photopheresis procedure. For example, decreased plasma clarity may be grounds for the system controller to adjust the amount of plasma used to suspend or re-suspend the MNCs or use a different fluid (e.g., saline) to dilute plasma-suspended MNCs.

(2) Adjusting Duration of MNC Harvest Phase

One aspect of an extracorporeal photopheresis procedure (or any other MNC collection procedure) that may be adjusted depending on (or independently of) plasma clarity is the duration of the MNC harvest phase.

Figure 14:
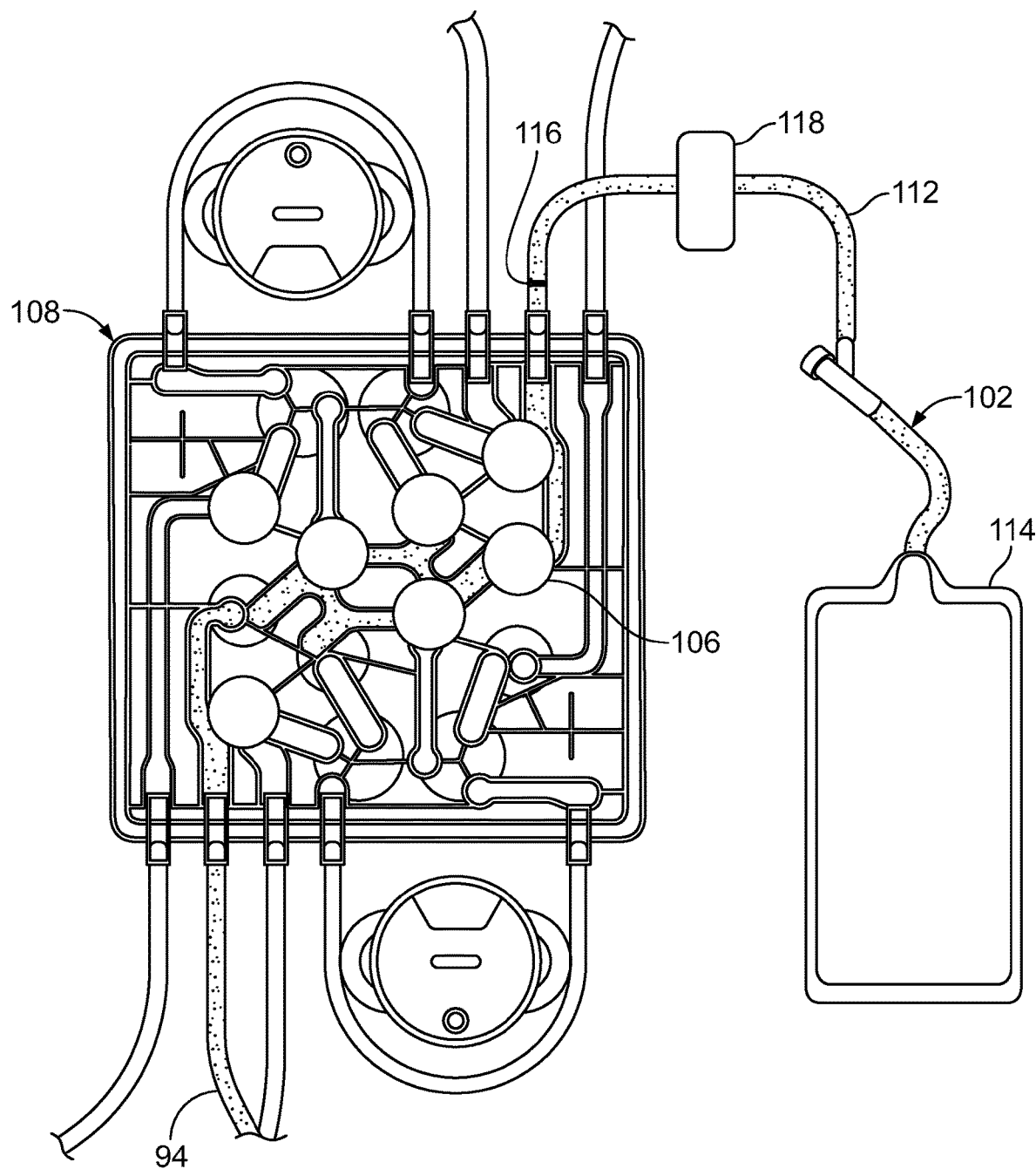
FIG. 14 is a detail view of a portion of the disposable fluid processing assembly of FIG. 13.

The system controller may be programmed with first and second offset volumes, which correspond to default times that determine when MNC collection begins and ends. The first offset volume (which is approximately 2.3 ml in one embodiment) is equal to the portion of the outlet flow path 102 (FIG. 14) defined by the fluid processing assembly 104 (FIG. 13) between the outlet optical sensor assembly 72 of the system 10 (which monitors flexible tubing 94 connected to the first outlet port 30) and a valve station 106 of a rigid cassette 108 of the fluid processing assembly 104 (FIG. 14). The cassette 108 and fluid processing assembly 104 may be provided generally in accordance with the description found in U.S. Pat. No. 5,462,416, which is incorporated herein by reference.

When the outlet optical sensor assembly 72 detects a transition from the plasma constituent to the MNC-containing layer, the volume of fluid in the outlet flow path 102 between the MNC-containing layer (i.e., at the outlet optical sensor assembly 72) and the valve station 106 is equal to the first offset volume, so the system controller allows a pump of the system 10 to operate to convey a volume of fluid equal to the first offset volume through the outlet flow path 102. By doing so, the pump has moved the MNC-containing layer through the outlet flow path 102 (i.e., through the tubing 94 and interior of the cassette 108) to the valve station 106 of the cassette 108. At that (default) time, the valve station 106 moves from a first condition to a second condition to change the direction of flow through the outlet flow path 102. In the first condition, the valve station 106 is arranged to direct fluid to a plasma constituent storage container 110 (FIG. 13), while directing fluid through a flexible tubing 112 to an MNC collection container 114 in the second condition (which is illustrated in FIG. 14).

The second offset volume (which is approximately 4.5 ml in one embodiment) is selected to approximate the volume of the MNC-containing layer that is collected during an individual harvest phase before the packed red blood cells being introduced into the first stage 24 begin approaching the tubing 112 leading to the mononuclear cell collection container 114. At this (default) time, at which the system controller moves the valve station 106 from the first condition to the second condition, the system controller allows a pump of the system 10 to operate to convey a volume of fluid equal to the second offset volume (i.e., the MNC-containing layer) through the outlet flow path 102 before closing flow to the mononuclear cell collection container 114. Subsequently, at the second default time, the harvest phase transitions back to the phase of building up the MNC-containing layer within the first stage 24 (i.e., by reopening the second outlet port 32 and drawing blood into the first stage 24 from the blood source). The phases of building up the MNC-containing layer within the first stage 24 and then harvesting the MNCs may be repeated until a target volume of blood has been processed or until the occurrence of some other event or condition (e.g., when a target volume of MNC product has been collected). Following collection, the MNC product may be treated to further processing, such as extracorporeal photopheresis.

During the harvest phase, an operator may adjust one or both offset volumes or default times if the operator determines that the offset volumes dictated by the system controller do not correspond with the collection goals of the operator and/or do not correspond to the content of the fluid exiting the first stage 24 via the first outlet port 30. For example, if the operator wishes to increase the amount of MNCs collected at the risk of also collecting platelets present in the plasma constituent or if the operator observes that the MNC-containing layer begins exiting the first stage 24 earlier than anticipated or detected by the system controller, then the operator may decrease the first offset volume (i.e., start directing the fluid flowing through the flow path the MNC collection container 114 sooner than dictated by the default first offset volume). If the operator wishes to decrease the risk of collecting platelets present in the plasma constituent or if the operator observes that the MNC-containing layer begins exiting the first stage 24 later than determined by the outlet optical sensor assembly 72 (e.g., due to the plasma constituent having decreased clarity), then the operator may increase the first offset volume (i.e., start directing the fluid flowing through the outlet flow path 102 to the mononuclear cell collection container 114 later than dictated by the default first offset volume). If the operator wishes to increase the amount of MNCs collected at the risk of also collecting red blood cells or if the operator observes that the MNC-containing layer has a greater volume than anticipated by the system controller, then the operator may increase the second offset volume (i.e., continue directing the fluid flowing through the outlet flow path102 to the mononuclear cell collection container 114 longer than dictated by the default second offset volume). If the operator wishes to decrease the risk of collecting red blood cells or if the operator observes that the MNC-containing layer has a smaller volume than anticipated by the system controller, then the operator may decrease the second offset volume (i.e., stop directing the fluid flowing through the outlet flow path 102 to the mononuclear cell collection container 114 before otherwise dictated by the default second offset volume).

Notably, in existing systems, any changes to one or both offset volumes or default times ordered by the operator only take effect during the subsequent cycle of a multi-cycle procedure, rather than being immediately implemented by the system controller. According to an aspect of the present disclosure, the system controller is programmed to initiate a change to one or both offset volumes or default times during the cycle in which the change was ordered by the operator (using a touchscreen or other user interface of the system 10), substantially instantaneously. The system controller may be further programmed to limit the changes ordered by the operator to predetermined ranges to prevent the operator from initiating or ending the harvest phase too early or too late. The system controller may be additionally programmed to either carry over the changes implemented by the operator to the MNC harvest phase of a subsequent cycle or to instead return one or both of the offset volumes to default values for the MNC harvest phase of a subsequent cycle.

(3) Determining when to End Harvest Phase

To aid the operator in determining when to end the MNC harvest phase, the outlet flow path 102 may include a visual marker or indicium 116 (FIG. 14). The visual marker or indicium 116 identifies a location in the outlet flow path 102 where the operator is to end the MNC harvest phase (i.e., close fluid communication between the outlet flow path 102 and the mononuclear cell collection container 114) when the red cells flowing through the outlet flow path 102 (behind the MNCs) reach the location identified by the visual marker or indicium 116. The visual marker or indicium 116 may identify a location of the upstream flexible tubing 94 of the outlet flow path 102, the cassette 108 of the outlet flow path 102, or (as in FIG. 14) the downstream flexible tubing 112 of the outlet flow path 102, depending on the configuration of the fluid processing assembly 104.

The exact configuration of the visual marker or indicium 116 may vary without departing from the scope of the present disclosure. In one embodiment, the visual marker or indicium 116 is a mark applied to or incorporated into the outlet flow path 102. It may be advantageous for the visual marker or indicium 116 to be a color other than red, which may be difficult to discern when red blood cells begin to approach the identified location or when the plasma is hemolytic. In another embodiment, the visual marker or indicium 116 is a separate component that is attached to the outlet flow path 102, which may be either fixedly or movably attached to the outlet flow path 102. A movable visual marker or indicium 116 may be advantageous to correctly pair the identified location with the flow rate of fluid through the outlet flow path 102. For example, if the flow rate through the outlet flow path 102 is relatively high, then it may be advantageous to move the visual marker or indicium 116 further upstream to account for a possible lag between the time that the operator sees the red blood cells reach the identified location and the time that the operator is able to stop the harvest phase. In yet another embodiment, the centrifuge hardware may be configured to apply the visual marker or indicium 116, such as by shining a light onto the outlet flow path 102 to identify a particular location.

It is also within the scope of the present disclosure for the outlet flow path 102 to include a plurality of visual markers or indicia 116. For example, there may be a plurality of visual markers or indicia 116 for different flow rates. In another embodiment, there may be a plurality of visual markers or indicia 116 that correspond to different offset volumes, if it is the intention of the operator to end the harvest phase after or before the typical cut-off point. If multiple visual markers or indicia 116 are provided, they may be either identically or differently configured.

(4) Preventing Contamination of MNC Product

If the operator does not end the harvest phase in time to prevent red blood cells from approaching the mononuclear cell collection container 114, the system controller or the operator may initiate a flow reversal in the outlet flow path 102 to prevent red blood cells from reaching the mononuclear cell collection container 114 (or at least minimize the amount of red blood cells reaching the mononuclear cell collection container 114) or to attempt to withdraw red blood cells from the mononuclear cell collection container 114.

According to one embodiment, the operator is primarily responsible for initiating reversal of flow through the outlet flow path 102. The operator observes the outlet flow path 102 during the MNC harvest phase and, if red blood cells flow past the valve station 106 (i.e., into the downstream flexible tubing 112), then the operator may command the system controller to reverse flow through the outlet flow path 102. The operator may instruct the system controller by using a touchscreen or keyboard or any other user interface of the system 10. The system controller responds to the instruction from the operator by controlling the responsible pump to reverse direction, thereby causing the red blood cells in the outlet flow path 102 to flow away from the mononuclear cell collection container 114. The red blood cells may be directed back into the blood separation chamber 22 or to some other location (e.g., returning the red blood cells to the blood source).

According to an alternative embodiment, the system 10 may be provided with a third optical sensor assembly 118 (FIGS. 13 and 14), which may be configured and oriented to monitor flow through the downstream flexible tubing 112. The third optical sensor assembly 118 (also referred to herein as the MNC optical sensor assembly) is configured to distinguish between the flow of MNCs and the flow of red blood cells, and may be configured generally in accordance with the foregoing description of the outlet optical sensor assembly 72. When the MNC optical sensor assembly 118 detects the transition from MNCs to red blood cells flowing through the flexible tubing 112, it generates an output or signal that is transmitted to the system controller. The system controller responds to the output or signal by controlling the responsible pump to reverse direction, thereby causing the red blood cells in the outlet flow path 102 to flow away from the mononuclear cell collection container 114. The red blood cells may be directed back into the blood separation chamber 22 or to some other location (e.g., returning the red blood cells to the blood source).

In addition to reversing the flow of fluid through the outlet flow path 102, the system controller may take any additional steps (e.g., changing the condition of one or more valve stations of the cassette 108) that may be required to prevent or reduce the presence of red blood cells in the mononuclear cell collection container 114.

Aspects

Aspect 1. A fluid processing system, comprising: a blood separation chamber configured to separate mononuclear cells from a plasma constituent of blood; an outlet flow path associated with the blood separation chamber for alternately removing at least a portion of said plasma constituent and at least a portion of said mononuclear cells from the blood separation chamber, wherein the outlet flow path includes a valve station movable between first and second conditions to change the direction of flow of fluid through the outlet flow path; a mononuclear cell collection container in fluid communication with the outlet flow path; and a controller programmed to execute a mononuclear cell collection procedure including a build-up phase in which said at least a portion of said plasma constituent flows through the outlet flow path and the controller causes the valve station to be in the first condition to direct the flow of said at least a portion of said plasma constituent through the outlet flow path away from the mononuclear cell collection container while a volume of the mononuclear cells increases in the blood separation chamber, and a harvest phase in which said at least a portion of said mononuclear cells flows through the outlet flow path and the controller causes the valve station to be in the second condition to direct the flow of said at least a portion of said mononuclear cells through the outlet flow path to the mononuclear cell collection container, wherein the controller is further programmed to allow an operator to selectively transition from the build-up phase to the harvest phase and/or from the harvest phase to the build-up phase substantially instantaneously.

Aspect 2. The fluid processing system of Aspect 1, wherein the mononuclear cell collection procedure executed by the controller includes a plurality of cycles of alternating said build-up and harvest phases.

Aspect 3. The fluid processing system of Aspect 2, wherein the controller is programmed with default times for transitioning from the build-up phase to the harvest phase and/or from the harvest phase to the build-up phase, and the controller is further programmed to transition from the build-up phase to the harvest phase at a time that is different from the default time for transitioning from the build-up phase to the harvest phase in a cycle based on the time at which the operator selectively transitioned from the build-up phase to the harvest phase during a previous cycle, and/or to transition from the harvest phase to the build-up phase at a time that is different from the default time for transitioning from the harvest phase to the build-up phase in a cycle based on the time at which the operator selectively transitioned from the harvest phase to the build-up phase during a previous cycle.

Aspect 4. The fluid processing system of Aspect 2, wherein the controller is programmed with default times for transitioning from the build-up phase to the harvest phase and/or from the harvest phase to the build-up phase, and the controller is further programmed to transition from the build-up phase to the harvest phase at the default time for transitioning from the build-up phase to the harvest phase in a cycle regardless of whether the operator selectively transitioned from the build-up phase to the harvest phase during a previous cycle, and/or to transition from the harvest phase to the build-up phase at the default time for transitioning from the harvest phase to the build-up phase in a cycle regardless of whether the operator selectively transitioned from the harvest phase to the build-up phase during a previous cycle.

Aspect 5. The fluid processing system of any one of the preceding Aspects, wherein the controller is programmed with default times for transitioning from the build-up phase to the harvest phase and/or from the harvest phase to the build-up phase, and the controller is further programmed to limit the ability of the operator to selectively transition from the build-up phase to the harvest phase and/or from the harvest phase to the build-up phase to predetermined ranges to prevent transitioning between phases at times that are too early or too late compared to the default times.

Aspect 6. The fluid processing system of any one of the preceding Aspects, wherein the outlet flow path is defined at least in part by a flexible tubing and a rigid cassette.

Aspect 7. The fluid processing system of Aspect 6, wherein the valve station is incorporated into the cassette.

Aspect 8. A method for collecting mononuclear cells, comprising: separating mononuclear cells from a plasma constituent of blood in a blood separation chamber; executing a build-up phase in which at least a portion of said plasma constituent flows out of the blood separation chamber via an outlet flow path with a valve station of the outlet flow path in a first condition to direct the flow of said at least a portion of said plasma constituent through the outlet flow path away from a mononuclear cell collection container in fluid communication with the outlet flow path while a volume of the mononuclear cells increases in the blood separation chamber; and executing a harvest phase in which at least a portion of said mononuclear cells flows out of the blood separation via the outlet flow path with the valve station in a second condition to direct the flow of said at least a portion of said mononuclear cells through the outlet flow path to the mononuclear cell collection container, wherein an operator is enabled to selectively transition from the build-up phase to the harvest phase and/or from the harvest phase to the build-up phase substantially instantaneously.

Aspect 9. The method of Aspect 8, further comprising a plurality of cycles of alternating said build-up and harvest phases.

Aspect 10. The method of Aspect 9, further comprising default times for automatically transitioning from the build-up phase to the harvest phase and/or from the harvest phase to the build-up phase, wherein the build-up phase automatically transitions to the harvest phase at a time that is different from the default time for transitioning from the build-up phase to the harvest phase in a cycle based on the time at which the operator selectively transitioned from the build-up phase to the harvest phase during a previous cycle, and/or the harvest phase automatically transitions to the build-up phase at a time that is different from the default time for transitioning from the harvest phase to the build-up phase in a cycle based on the time at which the operator selectively transitioned from the harvest phase to the build-up phase during a previous cycle.

Aspect 11. The method of Aspect 9, further comprising default times for automatically transitioning from the build-up phase to the harvest phase and/or from the harvest phase to the build-up phase, wherein the build-up phase automatically transitions to the harvest phase at the default time for transitioning from the build-up phase to the harvest phase in a cycle regardless of whether the operator selectively transitioned from the build-up phase to the harvest phase during a previous cycle, and/or the harvest phase automatically transitions to the build-up phase at the default time for transitioning from the harvest phase to the build-up phase in a cycle regardless of whether the operator selectively transitioned from the harvest phase to the build-up phase during a previous cycle.

Aspect 12. The method of any one of Aspects 8-11, further comprising default times for automatically transitioning from the build-up phase to the harvest phase and/or from the harvest phase to the build-up phase, wherein the ability of the operator to selectively transition from the build-up phase to the harvest phase and/or from the harvest phase to the build-up phase is limited to predetermined ranges to prevent transitioning between phases at times that are too early or too late compared to the default times.

Aspect 13. A fluid processing system, comprising: a blood separation chamber configured to separate a plasma constituent from another blood component and including an outlet port for removing at least a portion of the plasma constituent from the blood separation chamber; and a controller programmed to calculate an ideal plasma flow rate for said at least a portion of the plasma constituent flowing out of the blood separation chamber via the outlet port, compare the ideal plasma flow rate to a current plasma flow rate for said at least a portion of the plasma constituent flowing out of the blood separation chamber via the outlet port, determine that said at least a portion of the plasma constituent has decreased clarity if the percent difference between the ideal plasma flow rate and the current plasma flow rate is greater than a threshold value, and determine that said at least a portion of the plasma constituent does not have decreased clarity if the percent difference between the ideal plasma flow rate and the current plasma flow rate is less than the threshold value.

Aspect 14. The fluid processing system of Aspect 13, wherein the threshold value is approximately 25%.

Aspect 15. The fluid processing system of Aspect 13, wherein the threshold value is approximately 30%.

Aspect 16. The fluid processing system of Aspect 13, wherein the threshold value is approximately 20%.

Aspect 17. The fluid processing system of any one of Aspects 13-16, wherein the controller is further programmed to, upon determining that the plasma constituent has decreased clarity, automatically increasing the current plasma flow rate.

Aspect 18. The fluid processing system of any one of Aspects 13-16, wherein the controller is further programmed to, upon determining that the plasma constituent has decreased clarity, enable an operator to selectively increase the current plasma flow rate.

Aspect 19. The fluid processing system of Aspect 18, wherein the controller is further programmed to limit the amount that the operator may increase the current plasma flow rate.

Aspect 20. A method for separating blood, comprising: separating a plasma constituent from another blood component in a blood separation chamber; flowing at least a portion of said plasma constituent out of the blood separation chamber at a current plasma flow rate; calculating an ideal plasma flow rate for said at least a portion of the plasma constituent flowing out of the blood separation chamber; comparing the ideal plasma flow rate to the current plasma flow rate for said at least a portion of the plasma constituent flowing out of the blood separation chamber; determining that said at least a portion of the plasma constituent has decreased clarity if the percent difference between the ideal plasma flow rate and the current plasma flow rate is greater than a threshold value; and determining that said at least a portion of the plasma constituent does not have decreased clarity if the percent difference between the ideal plasma flow rate and the current plasma flow rate is less than the threshold value.

Aspect 21. The method of Aspect 20, wherein the threshold value is approximately 25%.

Aspect 22. The method of Aspect 20, wherein the threshold value is approximately 30%.

Aspect 23. The method of Aspect 20, wherein the threshold value is approximately 20%.

Aspect 24. The method of any one of Aspects 20-23, further comprising, upon determining that the plasma constituent has decreased clarity, automatically increasing the current plasma flow rate.

Aspect 25. The method of any one of Aspects 20-23, further comprising, upon determining that the plasma constituent has decreased clarity, enabling an operator to selectively increase the current plasma flow rate.

Aspect 26. The method of Aspect 25, wherein said enabling the operator to selectively increase the current plasma flow rate includes limiting the amount that the operator may increase the current plasma flow rate.

Aspect 27. A fluid processing assembly configured for use in combination with a fluid processing system for separating mononuclear cells from red blood cells, comprising: a blood separation chamber configured to separate mononuclear cells from red blood cells and including an outlet port configured to accommodate the flow of mononuclear cells and then red blood cells exiting the blood separation chamber; a mononuclear cell collection container; and an outlet flow path extending between the outlet port and the mononuclear cell collection container, wherein the outlet flow path includes a visual indicium upstream of the mononuclear cell collection container positioned to indicate that fluid communication between the outlet flow path and the mononuclear cell collection container is to be prevented upon red blood cells flowing through the outlet flow path reaching a location identified by the visual indicium.

Aspect 28. The fluid processing assembly of Aspect 27, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the upstream flexible tubing.

Aspect 29. The fluid processing assembly of Aspect 27, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the cassette.

Aspect 30. The fluid processing assembly of Aspect 27, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the downstream flexible tubing.

Aspect 31. A method for collecting mononuclear cells, comprising: separating mononuclear cells from red blood cells in a blood separation chamber; flowing at least a portion of said mononuclear cells out of the blood separation chamber via an outlet port, through an outlet flow path in fluid communication with the outlet port, and into a mononuclear cell collection container; flowing at least a portion of said red blood cells out of the blood separation chamber via the outlet port and into the outlet flow path; and preventing fluid communication between the outlet flow path and the mononuclear cell collection container when said at least a portion of said red blood cells flowing through the outlet flow path reaches a location identified by a visual indicium associated with the outlet flow path.

Aspect 32. The method of Aspect 31, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the upstream flexible tubing.

Aspect 33. The method of Aspect 31, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the cassette.

Aspect 34. The method of Aspect 31, wherein the outlet flow path is defined by a rigid cassette, an upstream flexible tubing extending between the outlet port and the cassette, and a downstream flexible tubing extending between the cassette and the mononuclear cell collection container, with the visual indicium identifying a location within the downstream flexible tubing.

Aspect 35. A fluid processing system, comprising: a blood separation chamber configured to separate mononuclear cells from red blood cells; an outlet flow path associated with the blood separation chamber and including a rigid cassette and a flexible tubing in fluid communication with the cassette, downstream of the cassette; a pump configured to convey fluid through the outlet flow path; a mononuclear cell optical sensor assembly configured to monitor the flow of fluid through the flexible tubing; a mononuclear cell collection container in fluid communication with the flexible tubing, downstream of the flexible tubing; and a controller programmed to control the operation of the pump and the mononuclear cell optical sensor assembly, wherein the mononuclear cell optical sensor assembly is configured to generate an output indicative of a transition from a flow of mononuclear cells through the flexible tubing toward the mononuclear cell collection container to a flow of red blood cells through the flexible tubing toward the mononuclear cell collection container, and the controller is programmed to receive the output and control the pump to reverse the direction of flow of fluid through the flexible tubing to minimize the amount of red blood cells reaching the mononuclear cell collection container.

Aspect 36. The fluid processing system of Aspect 35, further comprising an outlet optical sensor assembly configured to monitor the flow of fluid through the outlet flow path upstream of the cassette.

Aspect 37. A method for collecting mononuclear cells, comprising: separating mononuclear cells from red blood cells in a blood separation chamber; flowing at least a portion of said mononuclear cells out of the blood separation chamber via an outlet port, through a flexible tubing in fluid communication with the outlet port, and into a mononuclear cell collection container in fluid communication with the flexible tubing; flowing at least a portion of said red blood cells out of the blood separation chamber via the outlet port and into the flexible tubing; and reversing the direction of flow of said at least a portion of said red blood cells through the flexible tubing to minimize the amount of red blood cells reaching the mononuclear cell collection container.

Aspect 38. The method of Aspect 37, further comprising detecting the presence of said at least a portion of said red blood cells in the flexible tubing.

Aspect 39. The method of Aspect 38, further comprising optically detecting the presence of said at least a portion of said red blood cells in the flexible tubing.

Aspect 40. The method of any one of Aspects 37-39, wherein said reversing the direction of flow of said at least a portion of said red blood cells through the flexible tubing includes automatically initiating the reversal of the direction of flow.

Aspect 41. The method of any one of Aspects 37-39, wherein said reversing the direction of flow of said at least a portion of said red blood cells through the flexible tubing includes manually commanding a system controller of a fluid processing system to execute the reversal of the direction of flow.

Aspect 42. A method for collecting and treating mononuclear cells, comprising: separating mononuclear cells from a plasma constituent in a blood separation chamber; flowing at least a portion of said plasma constituent out of the blood separation chamber; determining whether the plasma constituent has decreased clarity; flowing at least a portion of said mononuclear cells out of the blood separation chamber and into a mononuclear cell collection container; and irradiating said at least a portion of said mononuclear cells in the mononuclear cell collection container with a dosage of light, wherein the dosage of light is equal to a default dosage if the plasma constituent does not have a decreased clarity and greater than the default dosage if the plasma constituent has decreased clarity.

Aspect 43. The method of Aspect 42, wherein said determining whether the plasma constituent has decreased clarity includes monitoring the light transmissivity of the plasma constituent.

Aspect 44. The method of Aspect 42, wherein said determining whether the plasma constituent has decreased clarity includes calculating an ideal plasma flow rate for said at least a portion of the plasma constituent flowing out of the blood separation chamber; comparing the ideal plasma flow rate to a current plasma flow rate for said at least a portion of the plasma constituent flowing out of the blood separation chamber; determining that said at least a portion of the plasma constituent has decreased clarity if the percent difference between the ideal plasma flow rate and the current plasma flow rate is greater than a threshold value; and determining that said at least a portion of the plasma constituent does not have decreased clarity if the percent difference between the ideal plasma flow rate and the current plasma flow rate is less than the threshold value.

Aspect 45. A fluid processing system, comprising: a blood separation chamber configured to separate mononuclear cells from a plasma constituent of blood; an outlet flow path associated with the blood separation chamber; a mononuclear cell collection container in fluid communication with the outlet flow path; an irradiation device configured to irradiate separated mononuclear cells in the mononuclear cell collection container; and a controller programmed to control the operation of the irradiation device and to determine whether the plasma constituent has decreased clarity, control the irradiation device to irradiate separated mononuclear cells in the mononuclear cell collection container with a default dosage of light if the plasma constituent does not have decreased clarity, and control the irradiation device to irradiate separated mononuclear cells in the mononuclear cell collection container with a dosage of light that is greater than the default dosage of light if the plasma constituent has decreased clarity.

Aspect 46. The fluid processing system of Aspect 45, further comprising an optical sensor assembly configured to monitor the light transmissivity of the plasma constituent and generate an output that is received by the controller for determining whether the plasma constituent has decreased clarity.

Aspect 47. The fluid processing system of Aspect 45, wherein the controller is programmed to determine whether the plasma constituent has decreased clarity by calculating an ideal plasma flow rate for said at least a portion of the plasma constituent flowing out of the blood separation chamber; comparing the ideal plasma flow rate to a current plasma flow rate for said at least a portion of the plasma constituent flowing out of the blood separation chamber; determining that said at least a portion of the plasma constituent has decreased clarity if the percent difference between the ideal plasma flow rate and the current plasma flow rate is greater than a threshold value; and determining that said at least a portion of the plasma constituent does not have decreased clarity if the percent difference between the ideal plasma flow rate and the current plasma flow rate is less than the threshold value.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing system, comprising:
a blood separation chamber configured to separate mononuclear cells from a plasma constituent of blood;
an outlet flow path associated with the blood separation chamber for alternately removing at least a portion of said plasma constituent and at least a portion of said mononuclear cells from the blood separation chamber, wherein the outlet flow path includes a valve station movable between first and second conditions to change the direction of flow of fluid through the outlet flow path;
a mononuclear cell collection container in fluid communication with the outlet flow path; and
a controller programmed to execute a mononuclear cell collection procedure including a build-up phase in which a volume of the mononuclear cells increases in the blood separation chamber and a harvest phase in which the mononuclear cells are flowed from the blood separation chamber to the mononuclear cell collection container, wherein
the harvest phase comprises a first stage in which said at least a portion of said plasma constituent flows through the outlet flow path and the controller causes the valve station to be in the first condition to direct a flow of said at least a portion of said plasma constituent away from the mononuclear cell collection container and a second stage in which said at least a portion of said mononuclear cells flows through the outlet flow path and the controller causes the valve station to be in the second condition to direct a flow of said at least a portion of said mononuclear cells through the outlet flow path to the mononuclear cell collection container,
the controller is programmed to allow an operator to selectively and substantially instantaneously transition from the first stage of the harvest phase to the second stage of the harvest phase, and
the controller is further programmed to allow an operator to selectively and substantially instantaneously end the second stage of the harvest phase.

2. The fluid processing system of claim 1, wherein the mononuclear cell collection procedure executed by the controller includes a plurality of cycles of alternating said build-up and harvest phases.

3. The fluid processing system of claim 2, wherein the controller is programmed with default times for transitioning from the first stage of the harvest phase to the second stage of the harvest phase and/or for ending the second stage of the harvest phase, and the controller is further programmed
to transition from the first stage of the harvest phase to the second stage of the harvest phase at a time that is different from the default time for transitioning from the first stage of the harvest phase to the second stage of the harvest phase in a cycle based on the time at which the operator selectively transitioned from the first stage of the harvest phase to the second stage of the harvest phase during a previous cycle, and/or
to end the second stage of the harvest phase at a time that is different from the default time for ending the second stage of the harvest phase in a cycle based on the time at which the operator selectively ended the second stage of the harvest phase during a previous cycle.

4. The fluid processing system of claim 2, wherein the controller is programmed with default times for transitioning from the first stage of the harvest phase to the second stage of the harvest phase and/or for ending the second stage of the harvest phase, and the controller is further programmed
to transition from the first stage of the harvest phase to the second stage of the harvest phase at the default time for transitioning from the first stage of the harvest phase to the second stage of the harvest phase in a cycle regardless of whether the operator selectively transitioned from the first stage of the harvest phase to the second stage of the harvest phase during a previous cycle, and/or
to end the second stage of the harvest phase at the default time for ending the second stage of the harvest phase in a cycle regardless of whether the operator selectively ended the second stage of the harvest phase during a previous cycle.

5. The fluid processing system of claim 1, wherein the controller is programmed with default times for transitioning from the first stage of the harvest phase to the second stage of the harvest phase and/or for ending the second stage of the harvest phase, and the controller is further programmed to limit the ability of the operator to selectively transition from the first stage of the harvest phase to the second stage of the harvest phase and/or to end the second stage of the harvest phase to predetermined ranges to prevent transitioning from the first stage of the harvest phase to the second stage of the harvest phase and/or ending the second stage of the harvest phase at times that are too early or too late compared to the default times.

6. The fluid processing system of claim 1, wherein the outlet flow path is defined at least in part by a flexible tubing and a rigid cassette.

7. The fluid processing system of claim 6, wherein the valve station is incorporated into the cassette.

8. A method for collecting mononuclear cells, comprising:
separating mononuclear cells from a plasma constituent of blood in a blood separation chamber;
executing a build-up phase in which a volume of the mononuclear cells increases in the blood separation chamber; and
executing a harvest phase comprising a first stage in which at least a portion of said plasma constituent flows via an outlet flow path with a valve station of the outlet flow path in a first condition to direct a flow of said at least a portion of said plasma constituent through the outlet flow path away from a mononuclear cell collection container in fluid communication with the outlet flow path and a second stage in which at least a portion of said mononuclear cells flows out of the blood separation via the outlet flow path with the valve station in a second condition to direct a flow of said at least a portion of said mononuclear cells through the outlet flow path to the mononuclear cell collection container, wherein an operator is enabled to selectively and substantially instantaneously transition from the first stage of the harvest phase to the second stage of the harvest phase and to selectively and substantially instantaneously end the second stage of the harvest phase.

9. The method of claim 8, further comprising a plurality of cycles of alternating said build-up and harvest phases.

10. The method of claim 9, further comprising default times for automatically transitioning from the first stage of the harvest phase to the second stage of the harvest phase and/or for ending the second stage of the harvest phase, wherein
the first stage of the harvest phase automatically transitions to the second stage of the harvest phase at a time that is different from the default time for transitioning from the first stage of the harvest phase to the second stage of the harvest phase in a cycle based on the time at which the operator selectively transitioned from the first stage of the harvest phase to the first stage of the harvest phase during a previous cycle, and/or the second stage of the harvest phase automatically ends at a time that is different from the default time for ending the second stage of the harvest phase in a cycle based on the time at which the operator selectively ended the second stage of the harvest phase during a previous cycle.

11. The method of claim 9, further comprising default times for automatically transitioning from the first stage of the harvest phase to the second stage of the harvest phase and/or for ending the second stage of the harvest phase, wherein the first stage of the harvest phase automatically transitions to the second stage of the harvest phase at the default time for transitioning from the first stage of the harvest phase to the second stage of the harvest phase in a cycle regardless of whether the operator selectively transitioned from the first stage of the harvest phase to the second stage of the harvest phase during a previous cycle, and/or the second stage of the harvest phase automatically ends at the default time for ending the second stage of the harvest phase in a cycle regardless of whether the operator selectively ended the second stage of the harvest phase during a previous cycle.

12. The method of claim 8, further comprising default times for automatically transitioning from the first stage of the harvest phase to the second stage of the harvest phase and/or for ending the second stage of the harvest phase, wherein the ability of the operator to selectively transition from the first stage of the harvest phase to the second stage of the harvest phase and/or to end the second stage of the harvest phase is limited to predetermined ranges to prevent transitioning from the first stage of the harvest phase to the second stage of the harvest phase and/or ending the second stage of the harvest phase at times that are too early or too late compared to the default times.

13. The fluid processing system of claim 1, wherein the blood separation chamber is further configured to separate said mononuclear cells from red blood cells, the harvest phase includes flowing said red blood cells through the outlet flow path after said at least a portion of said mononuclear cells has flowed through the outlet flow path, and the outlet flow path includes a visual indicium upstream of the mononuclear cell collection container positioned to indicate that fluid communication between the outlet flow path and the mononuclear cell collection container is to be prevented upon said red blood cells flowing through the outlet flow path reaching a location identified by the visual indicium.

14. The fluid processing system of claim 13, wherein the outlet flow path is defined by a cassette, an upstream flexible tubing extending between the cassette and an outlet port of the blood separation chamber, and a downstream flexible tubing extending between the cassette and the mononuclear cell collection container, with the visual indicium identifying a location within the upstream flexible tubing.

15. The fluid processing system of claim 13, wherein the outlet flow path is defined by a cassette, an upstream flexible tubing extending between the cassette and an outlet port of the blood separation chamber, and a downstream flexible tubing extending between the cassette and the mononuclear cell collection container, with the visual indicium identifying a location within the cassette.

16. The fluid processing system of claim 13, wherein the outlet flow path is defined by a cassette, an upstream flexible tubing extending between the cassette and an outlet port of the blood separation chamber, and a downstream flexible tubing extending between the cassette and the mononuclear cell collection container, with the visual indicium identifying a location within the downstream flexible tubing.

17. The fluid processing system of claim 1, further comprising an irradiation device configured to irradiate separated mononuclear cells in the mononuclear cell collection container, wherein the controller is further programmed to determine whether the plasma constituent has decreased clarity, control the irradiation device to irradiate said separated mononuclear cells in the mononuclear cell collection container with a default dosage of light when the plasma constituent does not have decreased clarity, and control the irradiation device to irradiate said separated mononuclear cells in the mononuclear cell collection container with a dosage of light that is greater than the default dosage of light when the plasma constituent has decreased clarity.

18. The fluid processing system of claim 1, further comprising a pump configured to convey fluid through the outlet flow path, and a mononuclear cell optical sensor assembly configured to monitor the flow of fluid through the outlet flow path, wherein the blood separation chamber is further configured to separate said mononuclear cells from red blood cells, the mononuclear cell optical sensor assembly is configured to generate an output indicative of a transition from a flow of said mononuclear cells through the outlet flow path toward the mononuclear cell collection container to a flow of said red blood cells through the outlet flow path toward the mononuclear cell collection container, and the controller is further programmed to receive the output and control the pump to reverse the direction of flow of fluid through the outlet flow path to minimize an amount of the red blood cells reaching the mononuclear cell collection container.

19. The fluid processing system of claim 1, wherein the blood separation chamber includes an outlet port for removing at least a portion of the plasma constituent from the blood separation chamber, and the controller is further programmed to calculate an ideal plasma flow rate for said at least a portion of the plasma constituent flowing out of the blood separation chamber via the outlet port, compare the ideal plasma flow rate to a current plasma flow rate for said at least a portion of the plasma constituent flowing out of the blood separation chamber via the outlet port, determine that said at least a portion of the plasma constituent has decreased clarity when a percent difference between the ideal plasma flow rate and the current plasma flow rate is greater than a threshold value, and determine that said at least a portion of the plasma constituent does not have decreased clarity when the percent difference between the ideal plasma flow rate and the current plasma flow rate is less than the threshold value.

20. The fluid processing system of claim 19, wherein the controller is further programmed to, upon determining that said at least a portion of the plasma constituent has decreased clarity, automatically increase the current plasma flow rate.

21. A fluid processing system, comprising:
- a blood separation chamber configured to separate mononuclear cells from a plasma constituent of blood;
- an outlet flow path associated with the blood separation chamber for alternately removing at least a portion of said plasma constituent and at least a portion of said mononuclear cells from the blood separation chamber, wherein the outlet flow path includes a valve station movable between first and second conditions to change the direction of flow of fluid through the outlet flow path;
- a mononuclear cell collection container in fluid communication with the outlet flow path; and
- a controller programmed to execute a mononuclear cell collection procedure including a build-up phase in which a volume of the mononuclear cells increases in the blood separation chamber and a harvest phase in which the mononuclear cells are flowed from the blood separation chamber to the mononuclear cell collection container, wherein the harvest phase comprises a first stage in which said at least a portion of said plasma constituent flows through the outlet flow path and the controller causes the valve station to be in the first condition to direct a flow of said at least a portion of said plasma constituent through the outlet flow path away from the mononuclear cell collection container and a second stage in which said at least a portion of said mononuclear cells flows through the outlet flow path and the controller causes the valve station to be in the second condition to direct a flow of said at least a portion of said mononuclear cells through the outlet flow path to the mononuclear cell collection container, the controller is programmed to allow an operator to selectively and substantially instantaneously increase a duration of the first stage of the harvest phase and/or a duration of the second stage of the harvest phase, and the controller is further programmed to allow an operator to selectively and substantially instantaneously decrease the duration of the first stage of the harvest phase and/or the duration of the second stage of the harvest phase.

\* \* \* \* \*